US011746107B2

(12) United States Patent
Witkowski et al.

(10) Patent No.: US 11,746,107 B2
(45) Date of Patent: Sep. 5, 2023

(54) PROCESS FOR THE PRODUCTION OF 5-(4-((2S,5S)-5-(4-CHLOROBENZYL)-2-METHYL-MORPHOLINO)PIPERIDIN-1-YL)-1H-1,2,4-TRIAZOL-3-AMINE

(71) Applicant: Molecure S.A., Warsaw (PL)

(72) Inventors: Grzegorz Witkowski, Warsaw (PL); Marta Magdycz, Chotomów (PL); Magdalena Tyszkiewicz, Warsaw (PL); Marcin Zakrzewski, Warsaw (PL); Stanislaw Pikul, Jaslo (PL)

(73) Assignee: Molecure S.A., Warsaw (PL)

( * ) Notice: Subject to any disclaimer, the term of this patent is extended or adjusted under 35 U.S.C. 154(b) by 0 days.

(21) Appl. No.: 17/032,232

(22) Filed: Sep. 25, 2020

(65) Prior Publication Data

US 2021/0147401 A1    May 20, 2021

Related U.S. Application Data

(60) Provisional application No. 62/905,494, filed on Sep. 25, 2019.

(30) Foreign Application Priority Data

Sep. 25, 2019 (PL) .......................................... 431269

(51) Int. Cl.
  *C07D 413/14*  (2006.01)
  *C07D 211/74*  (2006.01)
  *C07D 413/04*  (2006.01)

(52) U.S. Cl.
  CPC .......... *C07D 413/14* (2013.01); *C07D 211/74* (2013.01); *C07D 413/04* (2013.01)

(58) Field of Classification Search
  CPC ... C07D 413/14; C07D 211/74; C07D 413/04
  See application file for complete search history.

(56) References Cited

U.S. PATENT DOCUMENTS

| | | | |
|---|---|---|---|
| 9,440,953 B2 | 9/2016 | Golebiowski et al. | |
| 9,944,624 B2 | 4/2018 | Mazur et al. | |
| 10,208,020 B2 | 2/2019 | Mazur et al. | |
| 10,538,508 B2 | 1/2020 | Mazur et al. | |
| 2016/0297823 A1* | 10/2016 | Corman | C07D 401/04 |
| 2018/0228791 A1* | 8/2018 | Brown | A61K 31/4523 |
| 2021/0015822 A1 | 1/2021 | Mazur et al. | |

FOREIGN PATENT DOCUMENTS

WO        2017037670 A1        3/2017

OTHER PUBLICATIONS

Davidson; J. Chem. Soc., 1963, 3327-3333. https://doi.org/10.1039/JR9630003327 (Year: 1963).*
Kim; J. Org. Chem. 1985, 50, 11, 1927-1932. https://doi.org/10.1021/jo00211a028 (Year: 1985).*
Tilley; Helvetica Chimica Acta 1980, 63, 832-840. https://doi.org/10.1002/hlca.19800630411 (Year: 1980).*
Andryianau et al., "Discovery of OAT-1441—Highly Active, Selective and Orally Bioavailable Inhibitor of Human AMCase," OncoArendi Therapeutics (2019).
Andryianau et al., "Discovery of OAT-1441—Highly Potent, Selective and Orally Bioavailable Inhibitor of Human Acidic Mammalian Chitinase," OncoArendi Therapeutics (2018).
Andryianau, G. et al., Benzoxazepine-Derived Selective, Orally Bioavailable Inhibitor of Human Acidic Mammalian Chitinase *ACS Med. Chem. Lett.* 2020, 11, 1228-1235.
Bartoszewicz et al., "OATD-01, a dual hAMCase and hCHIT inhibitor as a potential therapeutic agent for treatment of pulmonary disease," Onco Arendi Therapeutics. (2019).
Bartoszewicz, "OAT-2068—A potent, selective, orally bioavailable inhibitor of mouse chitotriosidase and its efficacy in the bleomycin-induced pulmonary fibrosis model," OncoArendi Therapeutics (2019).
Borek et al., "Development of highly active acidic mammalian chitinase (AMCase) inhibitors of zwitterionic character," OncoArendi Therapeutics, (2018).
Borek et al., "OAT-2068—The first selective inhibitor of mouse chitotriosidase (mCHIT1)," OncoArendi Therapeutics (2018).
Czestkowski et al., "Discovery of OAT-2068—A potent, selective, orally bioavailable inhibitor of mouse chitotriosidase and its in vivo activity in the bleomycin-induced pulmonary fibrosis model in mice," OncoArendi Therapeutics (2019).
Czestkowski et al., "Pierwsky selecktywny inhibitor mysiej chitotriozydazy (mCHIT1)," OncoArendi Therapeutics (2017).
Dymek et al., "Dual AMCase/CHIT1 inhibitor OAT-899 reverses pulmonary inflammation and airway remodeling in two mice models of airway inflammation," OncoArendi Therapeutics (2017).
Dymek et al., "Ther therapeutic efficacy of OAT-889 (Dual AMCase/CHIT1 Inhibitor) in comparison to montelukast in HDM-induced model of chronic airway inflammation in mice," Onco Arendi Therapeutics. (2017).
Gruzo et al., "Benzoxazepine derived OAT-1441 as selective orally bioavailable inhibitor of human acidic mammalian chitinase (hAMCase)," Onco Arendi Therapeutics. (2020).
Koralewski, R. et.al., Discovery of OATD-01, a First-in-Class Chitinase Inhibitor as Potential New Therapeutics for Idiopathic Pulmonary Fibrosis *J. Med. Chem.* 2020, 63, 24, 15527-15540.
Kowalski et al., "Discovery of an advanced dual chitinase inhibitor OAT-870: A new potential therapeutic in therapy of lung diseasds," OncoArendi Therapeutics (2019).
Lipner et al., "Phase 1, first-in human study of OATD-01, a dual chitinase inhibitor," Onco Arendi Therapeutics (2018).
Mazur et al., "Development of dual AMCase and CHIT1 inhibitor OAT-870 as a potential therapeutic for interstitial lung diseases," Onco Arendi Therapeutics, (2018).

(Continued)

*Primary Examiner* — Daniel R Carcanague
(74) *Attorney, Agent, or Firm* — Dana M. Gordon; Laura A. Wzorek; Foley Hoag LLP

(57) ABSTRACT

The present invention relates to a process for the synthesis of 5-(4-((2S,5S)-5-(4-chlorobenzyl)-2-methylmorpholino) piperidin-1-yl)-1H-1,2,4-triazol-3-amine in two hydrated crystalline forms and in one anhydrous crystalline form. The present invention further relates to methyl (Z)-4-((2S,5S)-5-(4-chlorobenzyl)-2-methylmorpholino)-N-cyanopiperidine-1-carbimidothioate which is an intermediate in this process.

14 Claims, 18 Drawing Sheets

(56) References Cited

OTHER PUBLICATIONS

Mazur et al., "Development of dual chitinase inhibitors as potential new treatment for respiratory system diseases," J Med Chem, 62:7126-7145 (2019).

Mazur et al., "Development of potent, in vivo active, acidic mammalian chitinase inhibitors as potential therapeutics for asthma," Onco Arendi Therapeutics (2017).

Mazur et al., "Discovery of selective, orally bioavailable inhibitor of mouse chitotriosidase," Bioorganic & Medicinal Chemistry Letters, 28:310-314 (2018).

Mazur et al., "OATD-01—orally bioavailable, dual chitinase inhibitor as a potential therapy for interstitial lung diseases," Onco Arendi Therapeutics (2019).

Mazur et al., "Targeting acidic mammalian chitinase is effective in animal model of asthma," J Med Chem, 61:695-710 (2018).

Niedsiejko et al., "Development of OAT-870—Dual CHIT1 and amcase inhibitor effective in HDM-induced allergic airway inflammation mouse model," Onco Arendi Therapeutics, (2019).

Niedsiejko et al., "Discovery of selective, orally bioavailable inhibitor of human acidic mammalian chitnase," Onco Arendi Therapeutics, (2018).

Sklepkiewicz et al., "Clinical Development of OATD-01: a Novel Chitinase Inhibitor for Treatment of Interstitial Lung Diseases," Onco Arendi Therapeutics (2019).

Sklepkiewicz et al., "OATD-01, a dual chitinase inhibitor, significantly ameliorates pulmonary fibrosis in the bleomycin-induced mouse model," Onco Arendi Therapeutics (2018).

Sklepkiewicz et al., "XHIT1 is a novel therapeutic target in IPF: anti-fibrotic efficacy of OATD-01, a potent and selective chitinase inhibitor, in the mouse model of pulmonary fibrosis," Onco Arendi Therapeutics, (2018).

International Search Report and Written Opinion issued in PCT/IB2020/058984, dated Feb. 9, 2021, pp. 1-19.

Ramtohul, et al. "Bicyclic heteroaryl inhibitors of stearoly-CoA desaturase: From systemic to liver-targeting inhibitors," Bioorganic & Medicinal Chemistry Letters, vol. 21, No. 19, 2011, pp. 5692-5696.

* cited by examiner

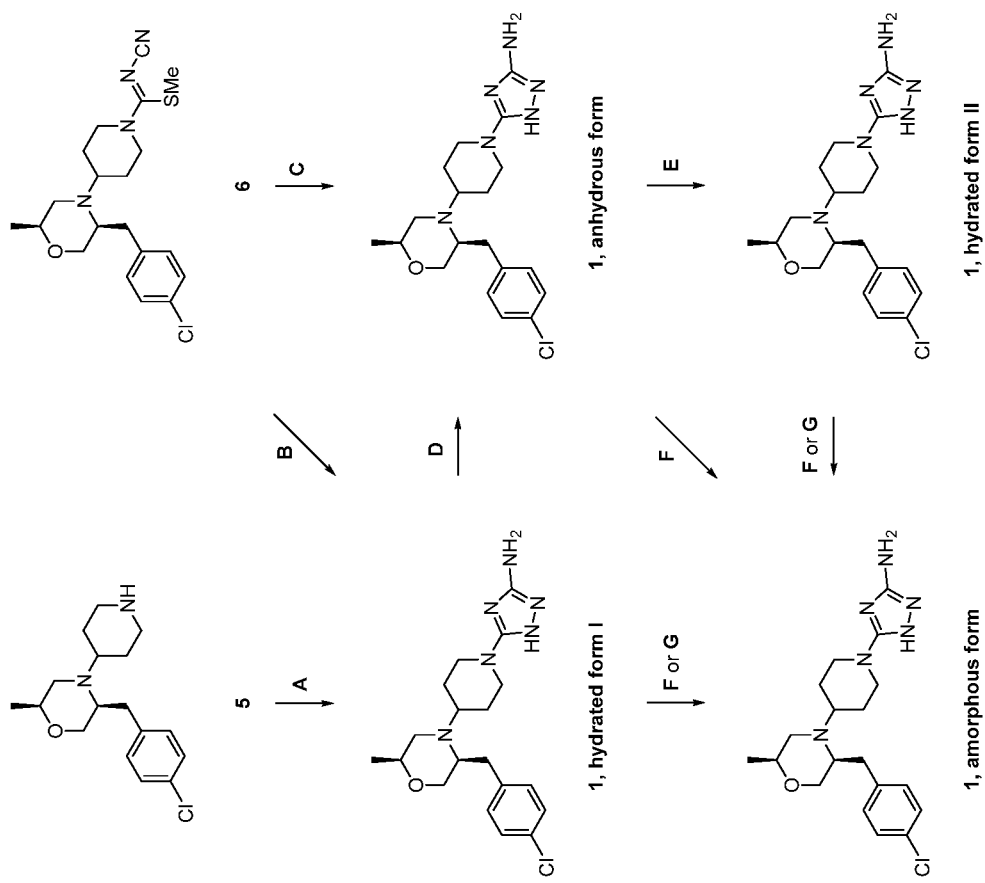
FIG. 1. Scheme of the synthesis of various forms of 5-(4-((2S,5S)-5-(4-chlorobenzyl)-2-methylmorpholino)piperidin-1-yl)-1H-1,2,4-triazol-3-amine.

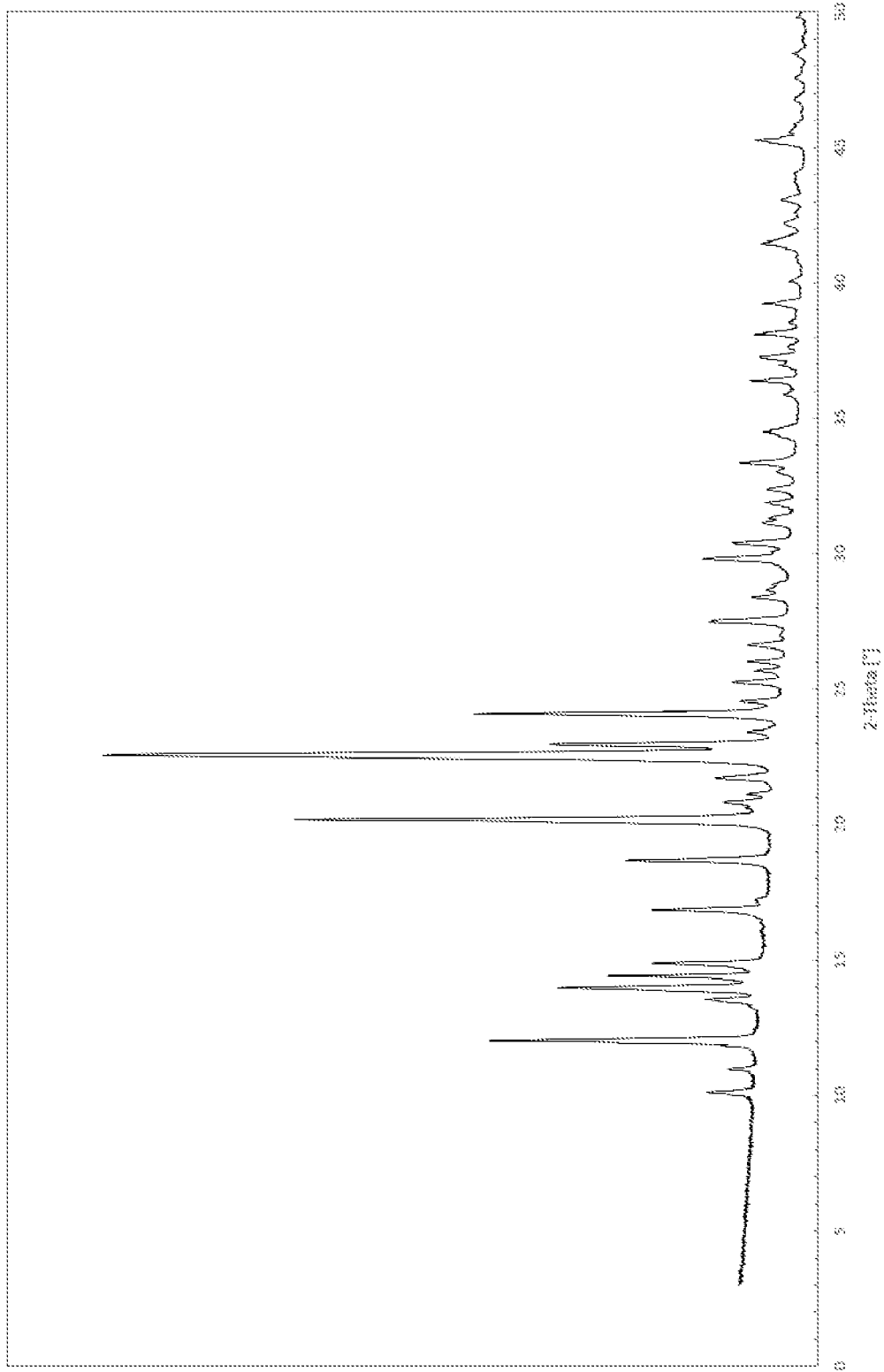
FIG. 2. XPRD diffractogram of methyl (Z)-4-((2S,5S)-5-(4-chlorobenzyl)-2-methylmorpholino)-N-cyanopiperidine-1-carbimidothioate obtained in Example 3.

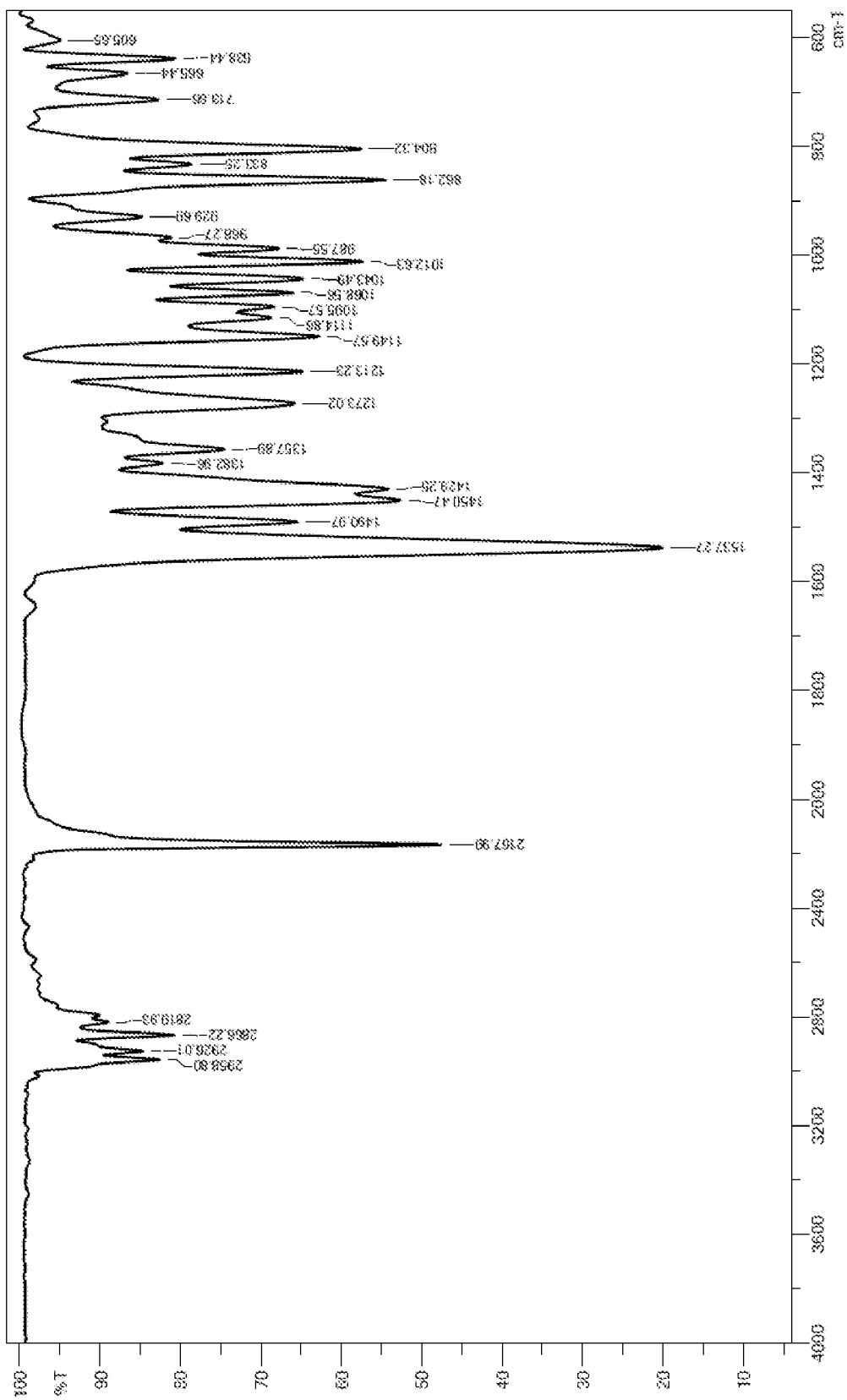
FIG. 3. FT-IR (ATR) spectrum of methyl (Z)-4-((2S,5S)-5-(4-chlorobenzyl)-2-methylmorpholino)-N-cyanopiperidine-1-carbimidothioate obtained in Example 3.

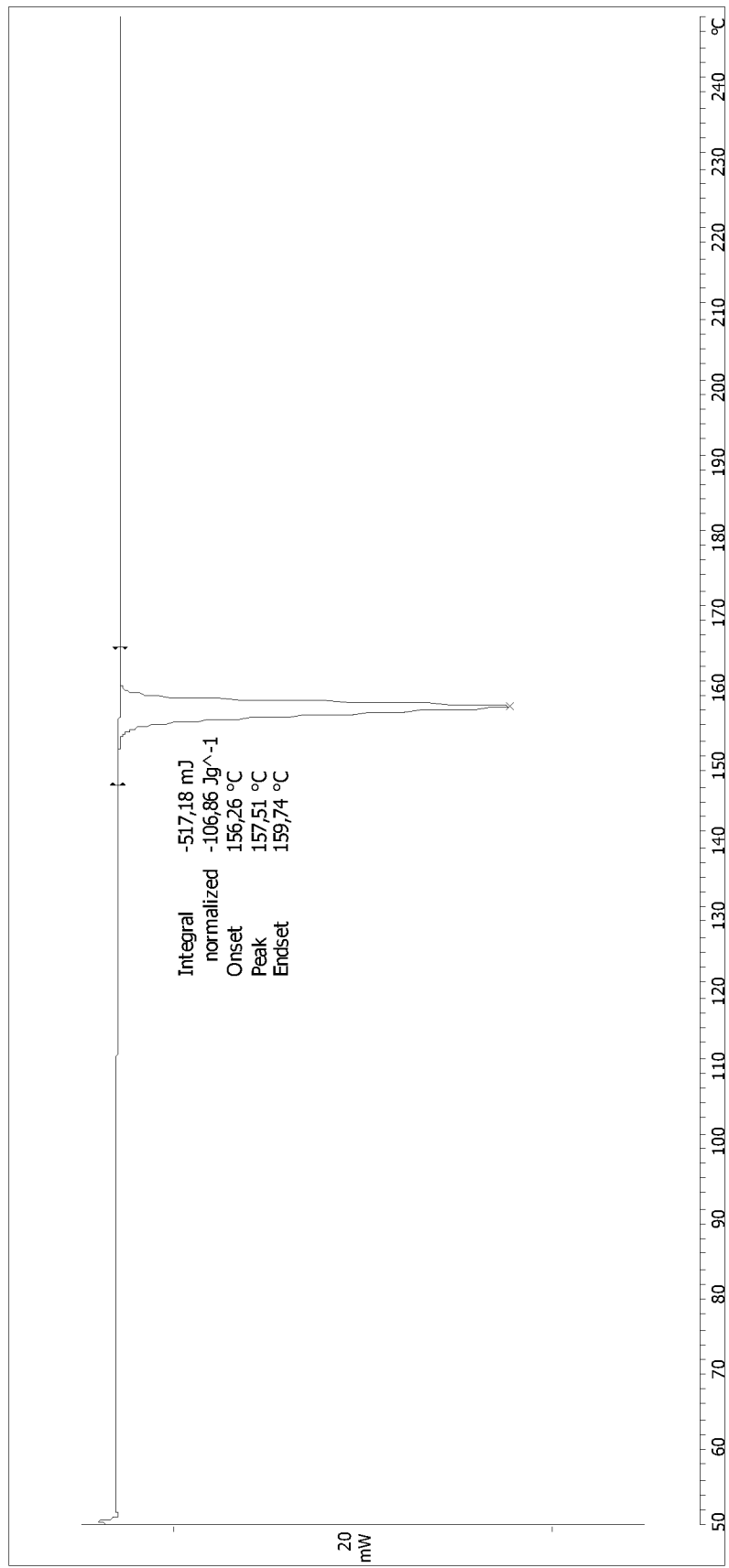
FIG. 4. DSC thermogram of methyl (Z)-4-((2S,5S)-5-(4-chlorobenzyl)-2-methylmorpholino)-N-cyanopiperidine-1-carbimidothioate obtained in Example 3.

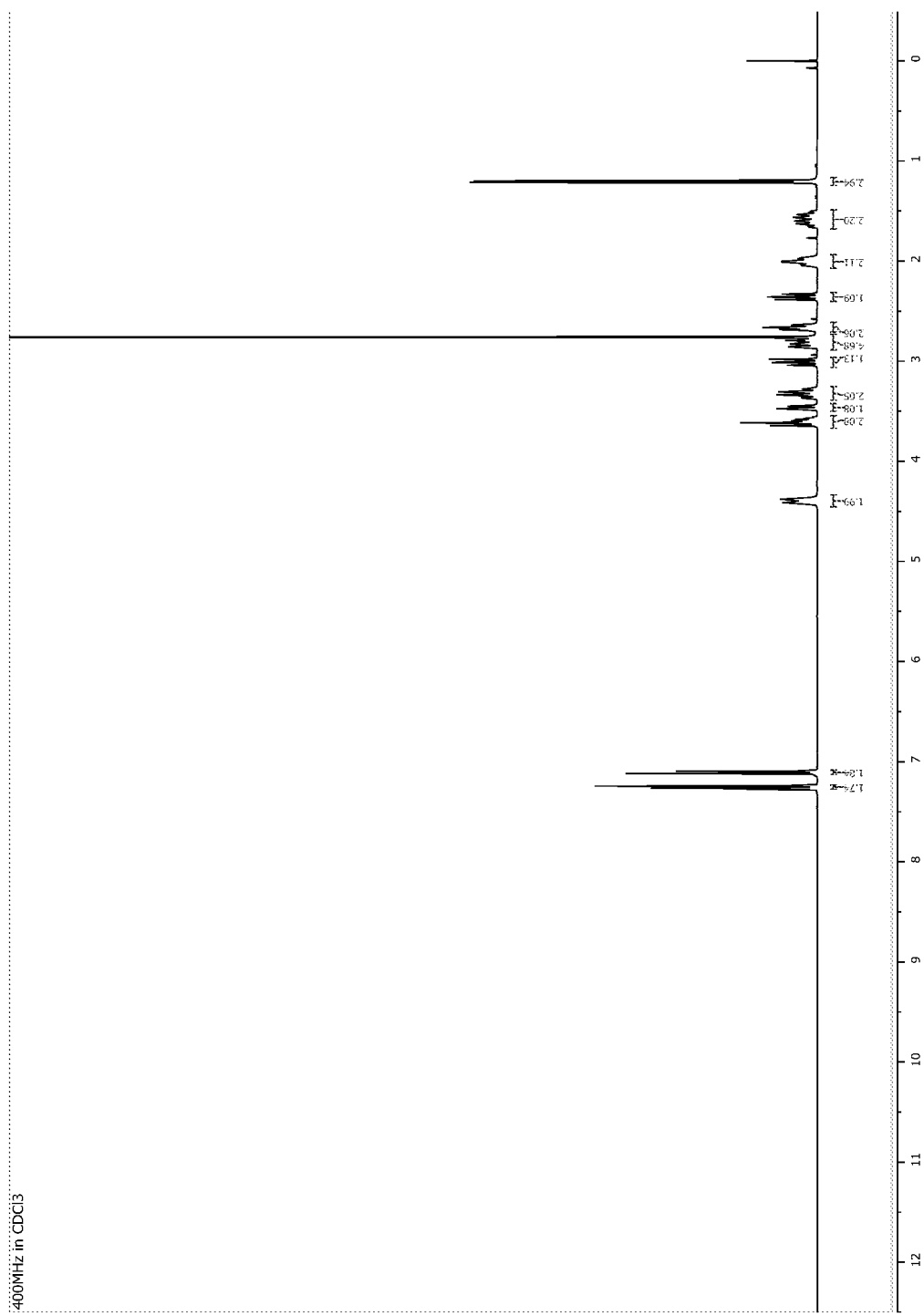
FIG. 5. $^1$H NMR spectrum (CDCl$_3$ at 400 MHz) of methyl (Z)-4-((2S,5S)-5-(4-chlorobenzyl)-2-methylmorpholino)-*N*-cyanopiperidine-1-carbimidothioate obtained in Example 3.

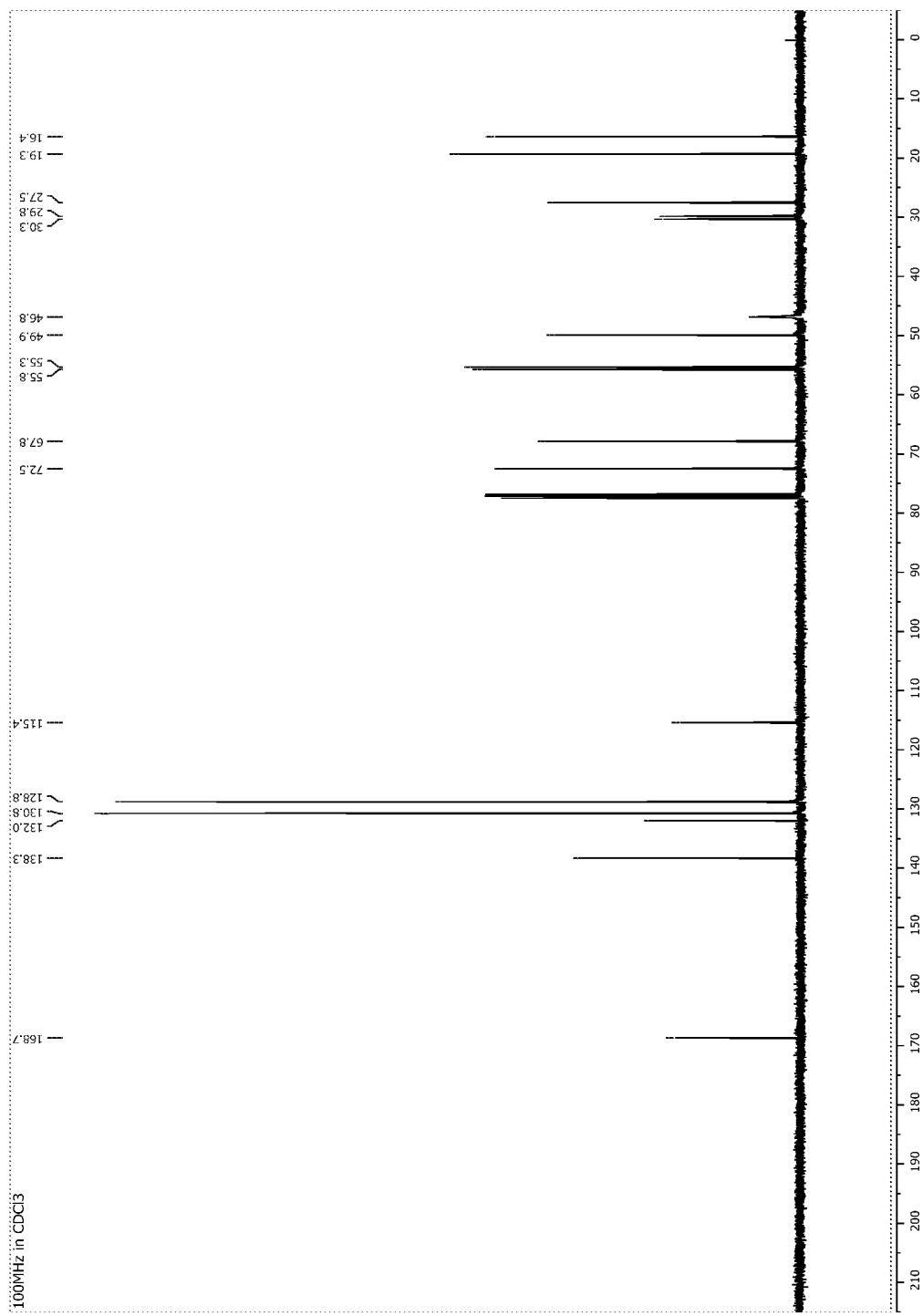
FIG. 6. $^{13}$C NMR spectrum (CDCl$_3$ at 100 MHz) of methyl (Z)-4-((2S,5S)-5-(4-chlorobenzyl)-2-methylmorpholino)-N-cyanopiperidine-1-carbimidothioate obtained in Example 3.

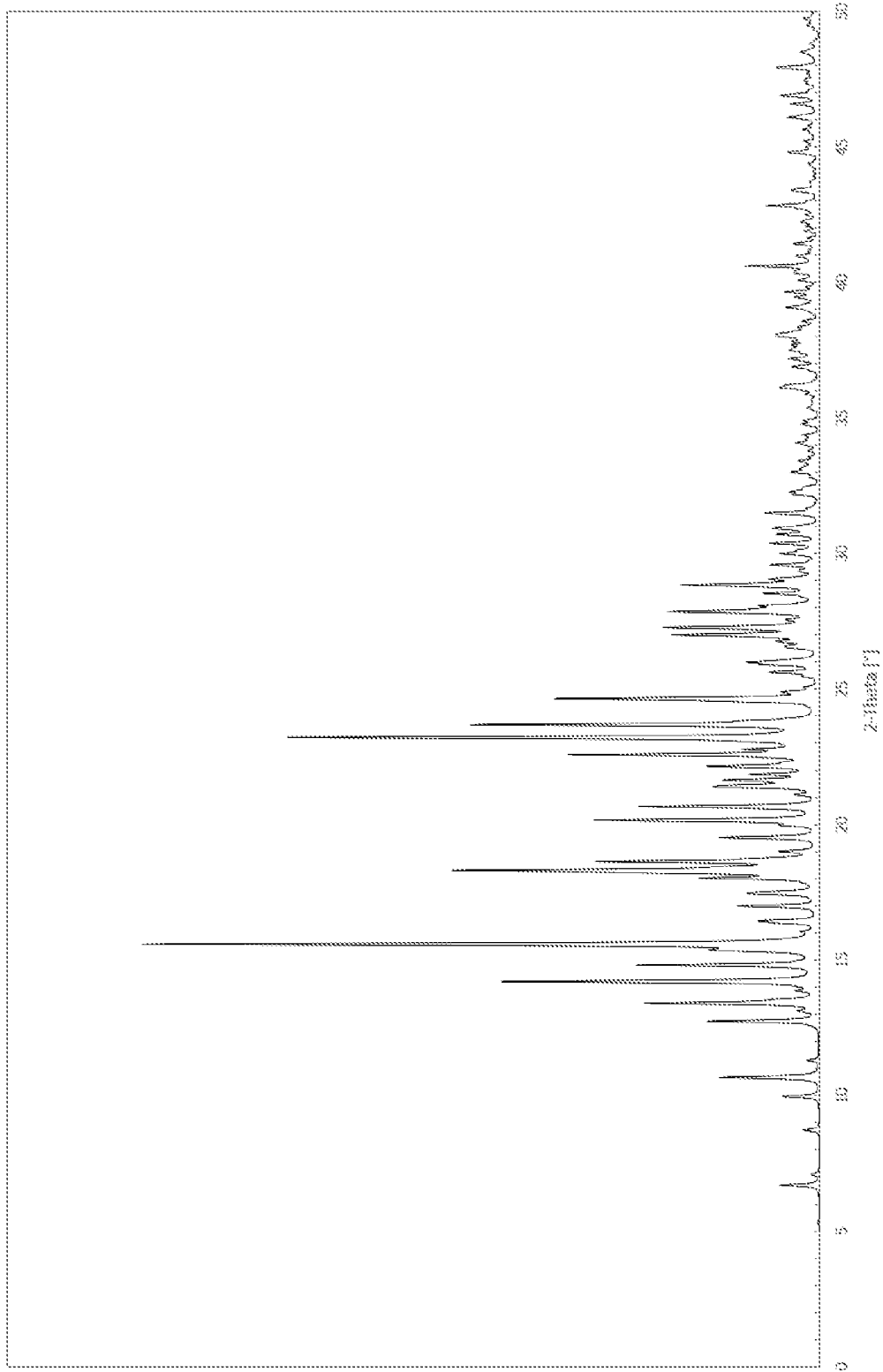
FIG. 7. XPRD diffractogram of 5-(4-((2S,5S)-5-(4-chlorobenzyl)-2-methylmorpholino)piperidin-1-yl)-1H-1,2,4-triazol-3-amine hydrated form I calculated from X-ray analysis of a single crystal obtained from a mixture of water and ethanol.

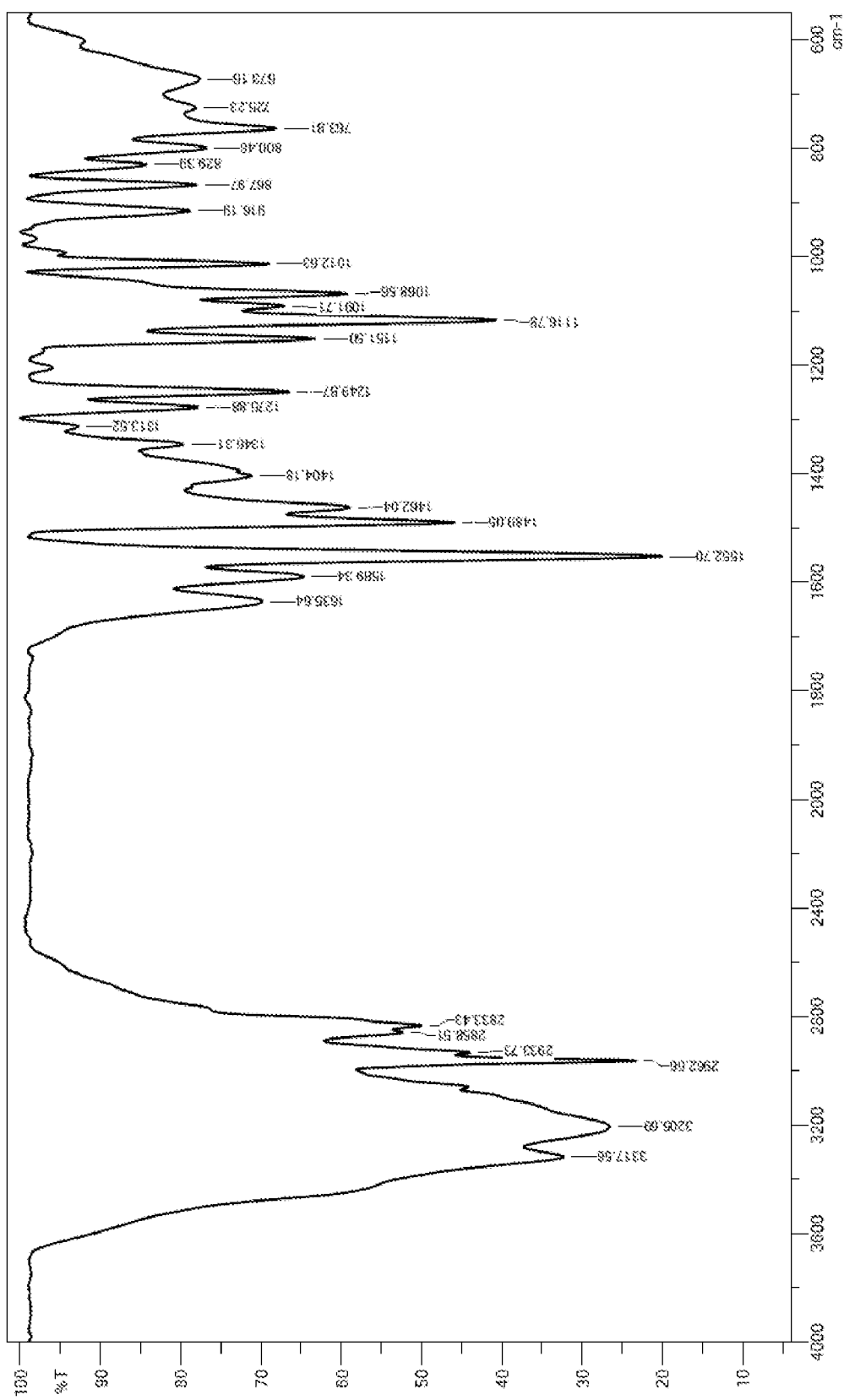
FIG. 8. FT-IR (ATR) spectrum of 5-(4-((2S,5S)-5-(4-chlorobenzyl)-2-methylmorpholino)piperidin-1-yl)-1H-1,2,4-triazol-3-amine hydrated form I obtained in Example 6.

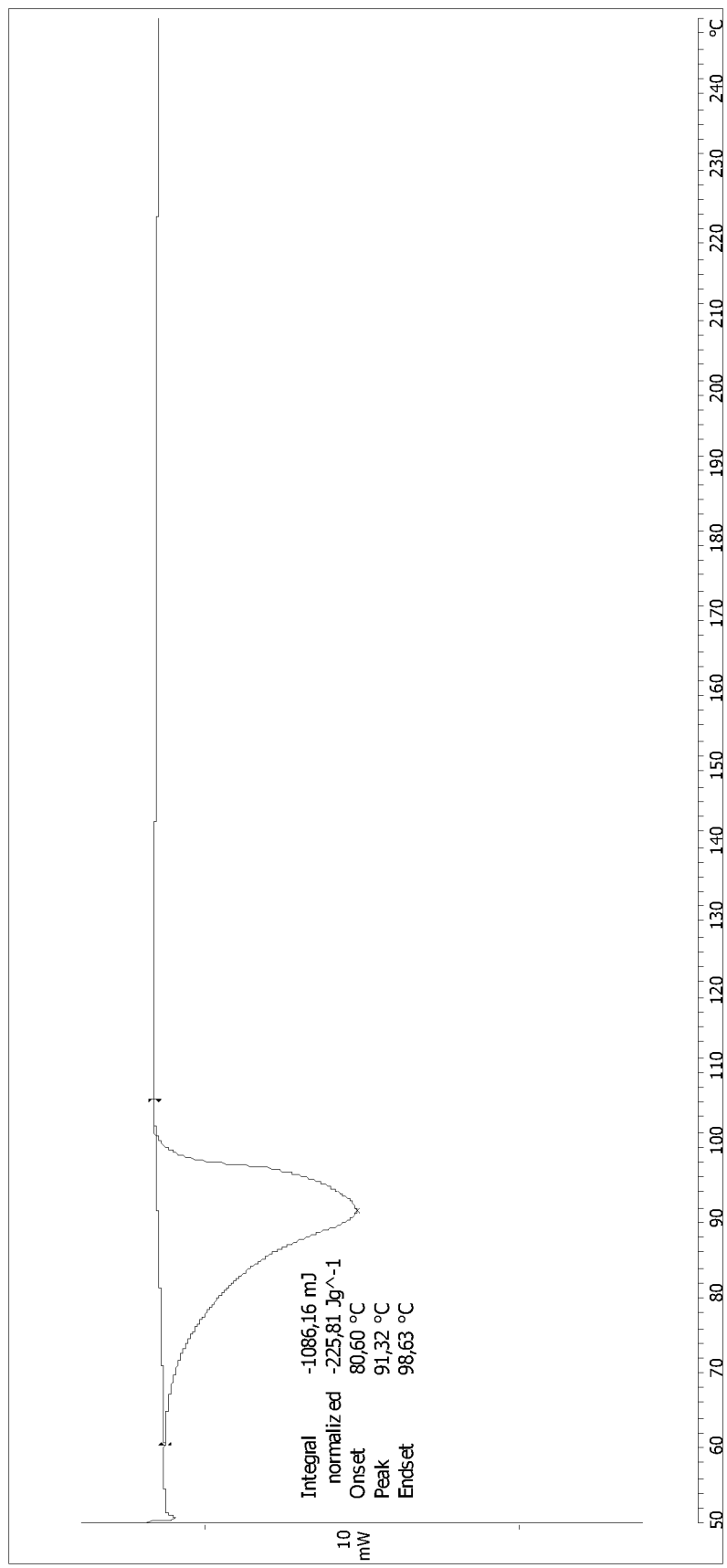
FIG. 9. DSC thermogram of 5-(4-((2S,5S)-5-(4-chlorobenzyl)-2-methylmorpholino)piperidin-1-yl)-1H-1,2,4-triazol-3-amine hydrated form I obtained in Example 6.

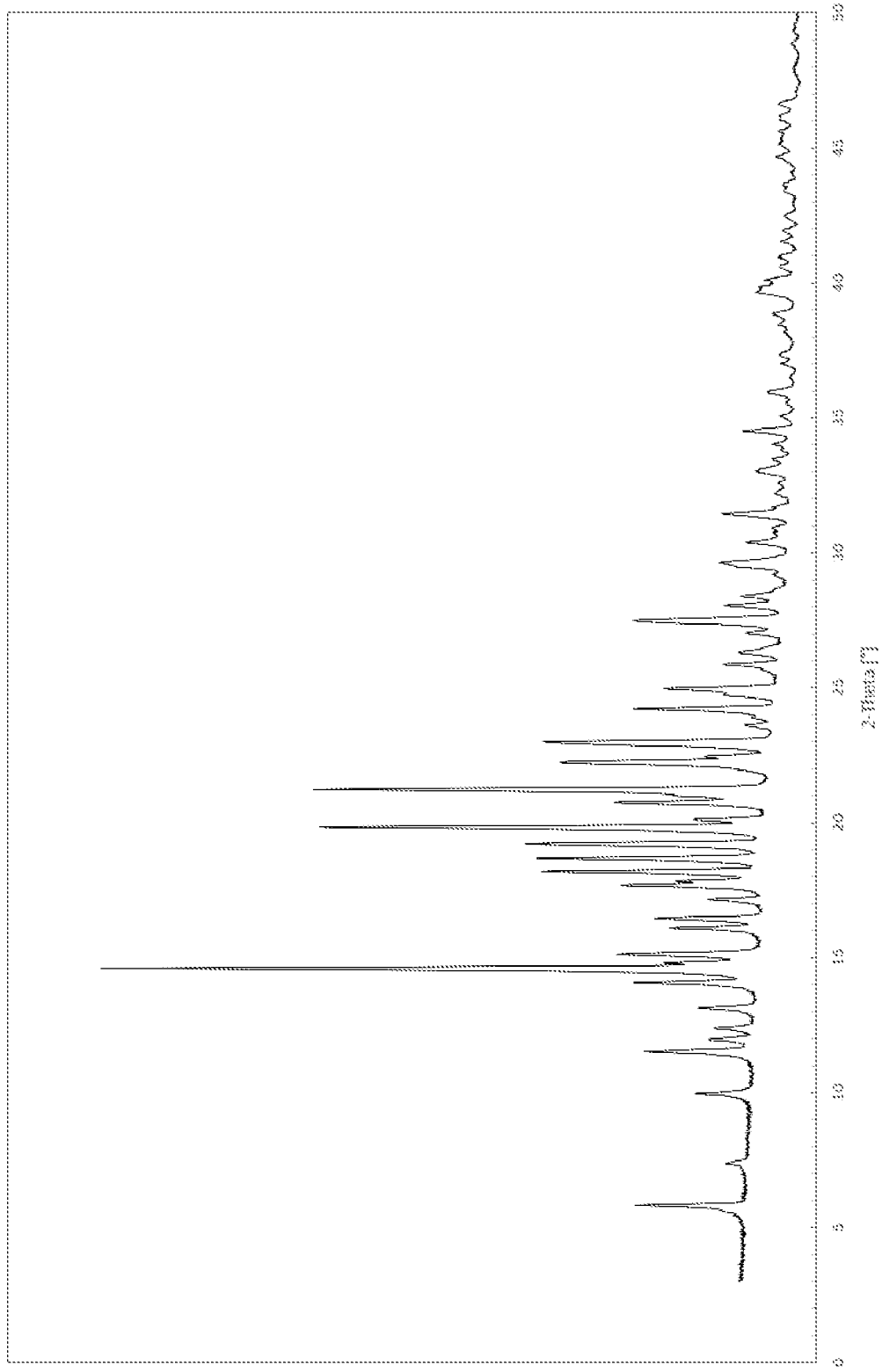
FIG. 10. XPRD diffractogram of 5-(4-((2S,5S)-5-(4-chlorobenzyl)-2-methylmorpholino)piperidin-1-yl)-1H-1,2,4-triazol-3-amine anhydrous form obtained in Example 8.

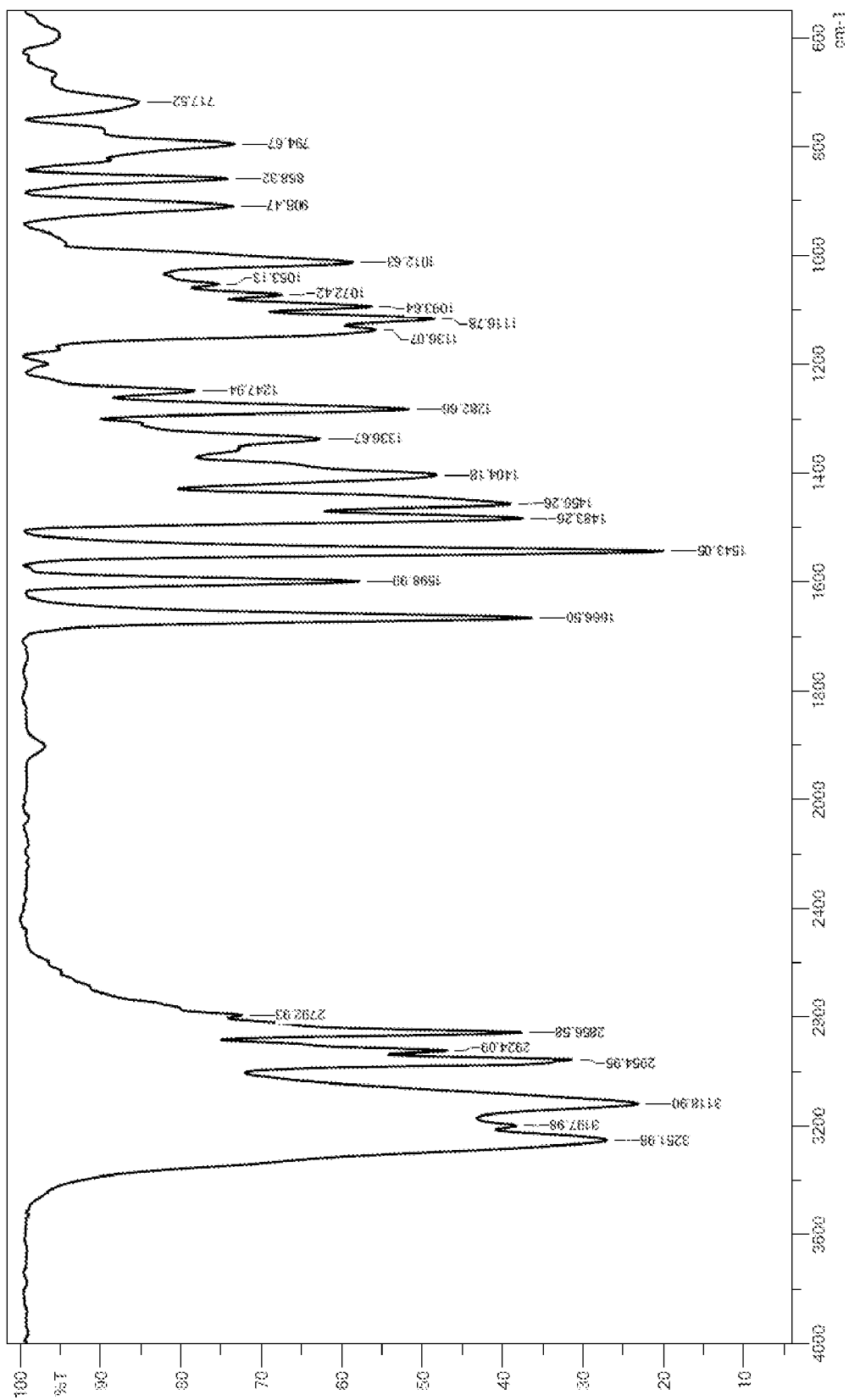
FIG. 11. FT-IR (ATR) spectrum of 5-(4-((2S,5S)-5-(4-chlorobenzyl)-2-methylmorpholino)piperidin-1-yl)-1H-1,2,4-triazol-3-amine anhydrous form obtained in Example 8.

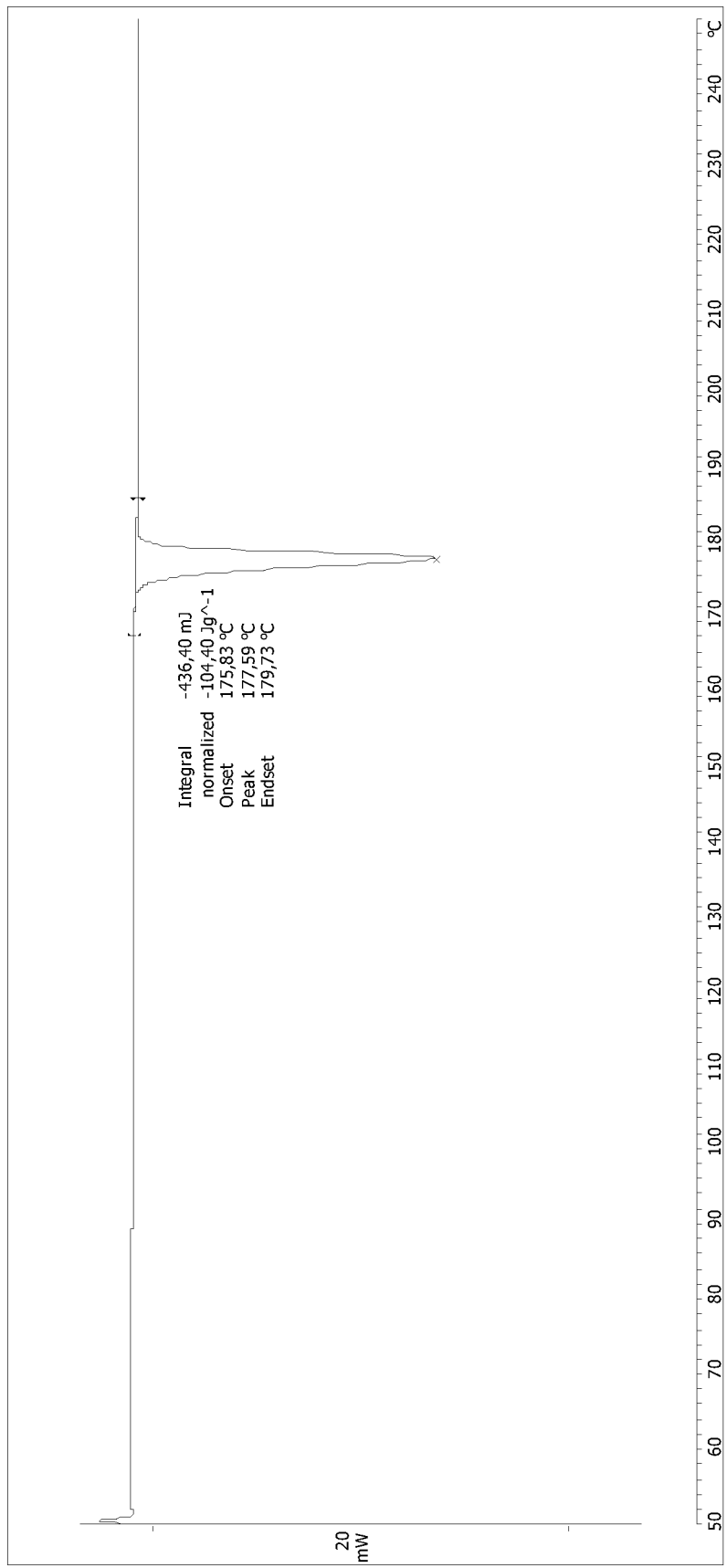
FIG. 12. DSC thermogram of 5-(4-((2S,5S)-5-(4-chlorobenzyl)-2-methylmorpholino)piperidin-1-yl)-1H-1,2,4-triazol-3-amine anhydrous form obtained in Example 8.

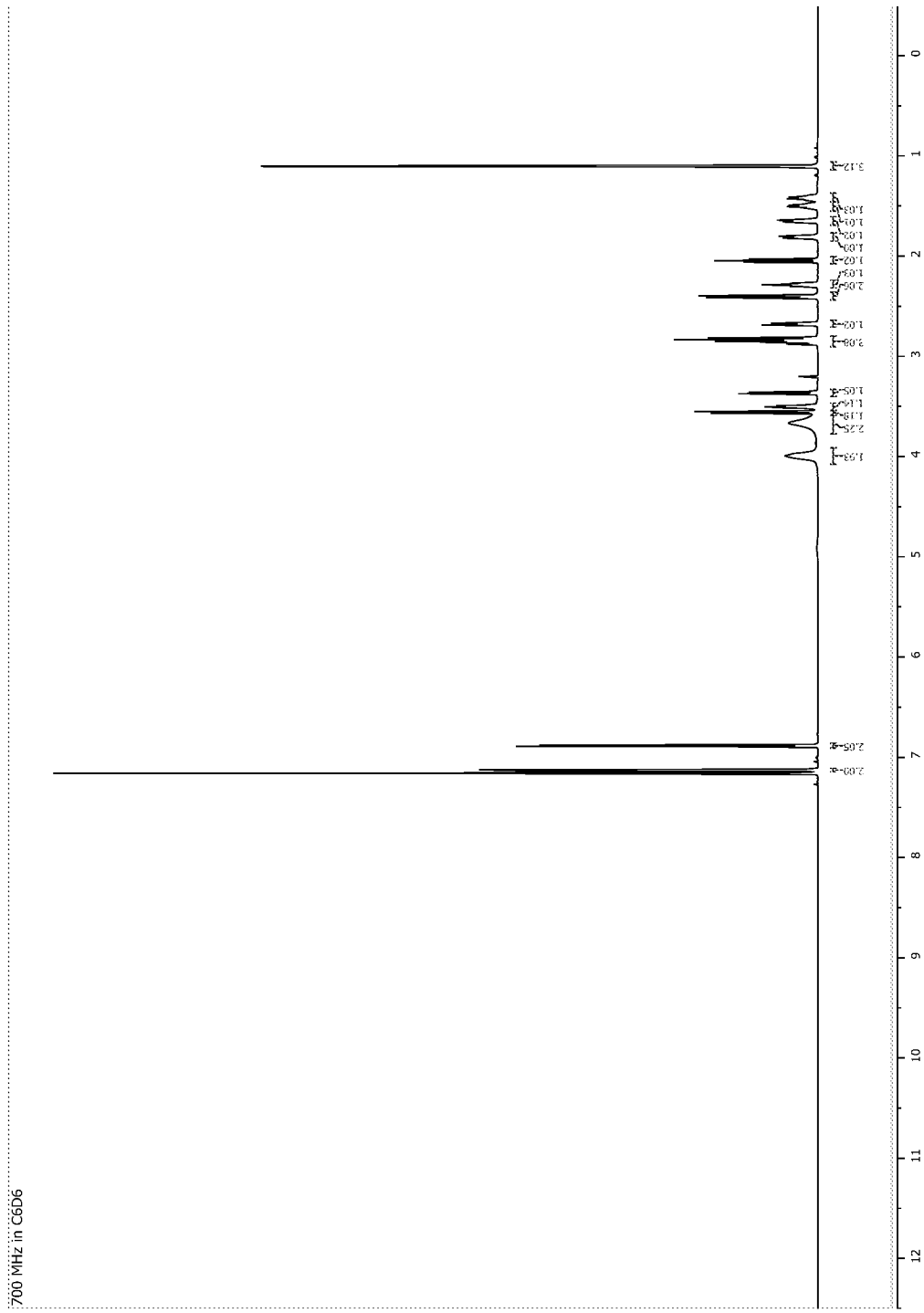
FIG. 13. $^1$H NMR (C$_6$D$_6$ at 700 MHz) spectrum of 5-(4-(((2S,5S)-5-(4-chlorobenzyl)-2-methylmorpholino)piperidin-1-yl)-1H-1,2,4-triazol-3-amine anhydrous form obtained in Example 8.

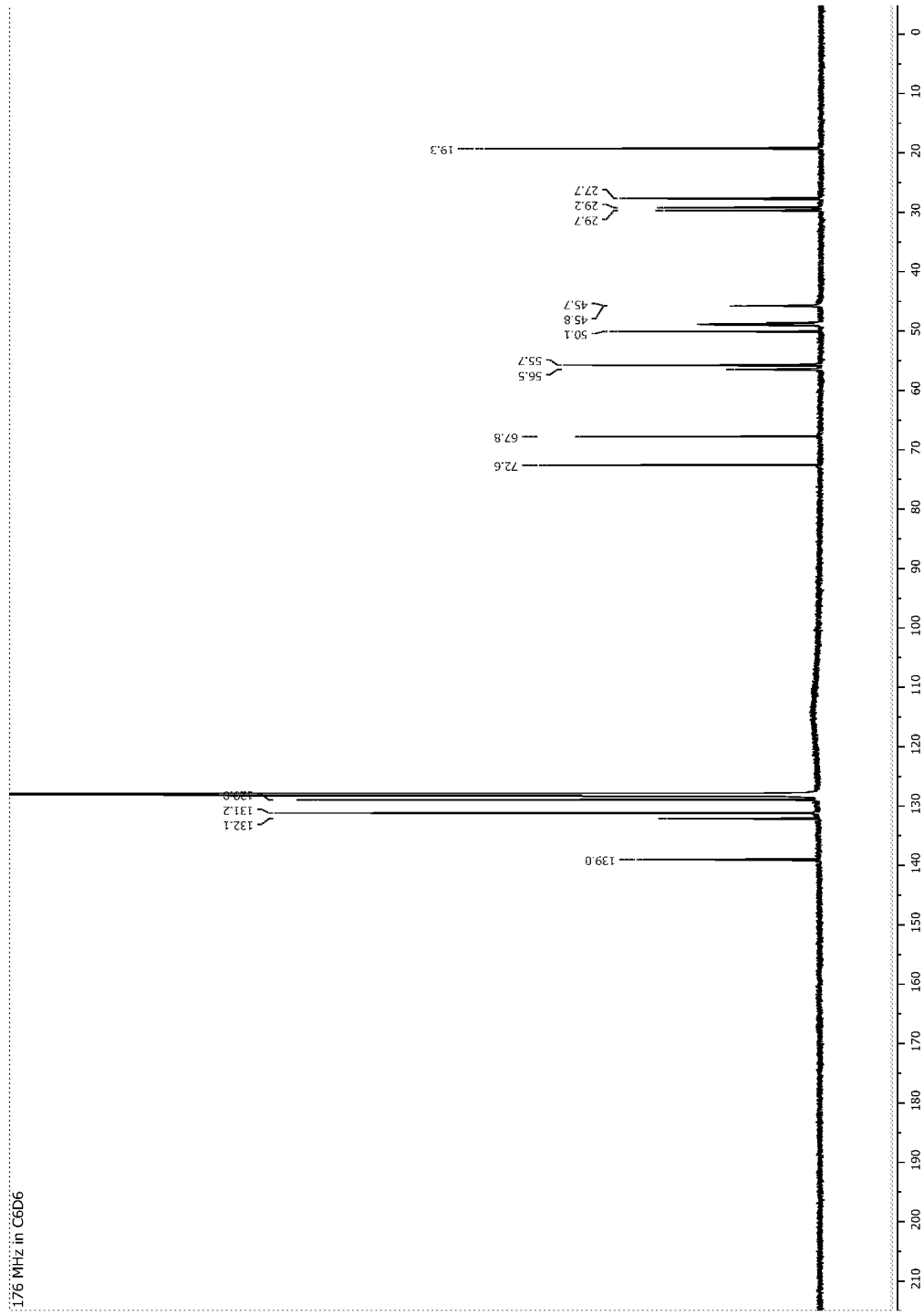
FIG. 14. $^{13}$C NMR (C$_6$D$_6$ at 176 MHz) spectrum of 5-(4-((2S,5S)-5-(4-chlorobenzyl)-2-methylmorpholino)piperidin-1-yl)-1H-1,2,4-triazol-3-amine anhydrous form obtained in Example 8.

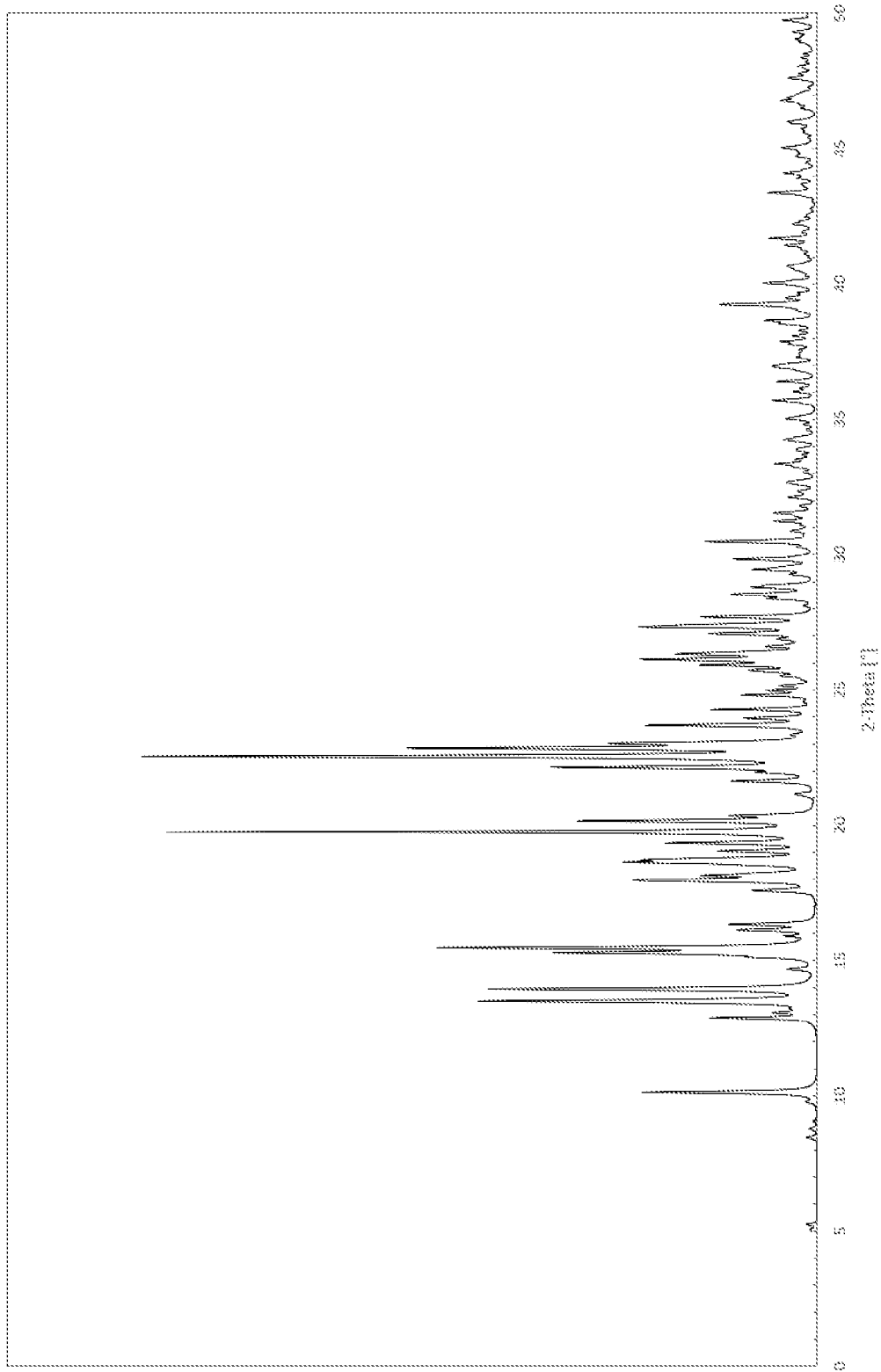
FIG. 15. XPRD diffractogram of 5-(4-(((2S,5S)-5-(4-chlorobenzyl)-2-methylmorpholino)piperidin-1-yl)-1H-1,2,4-triazol-3-amine hydrated form II calculated from X-ray analysis of a single crystal obtained from a mixture of water and methanol.

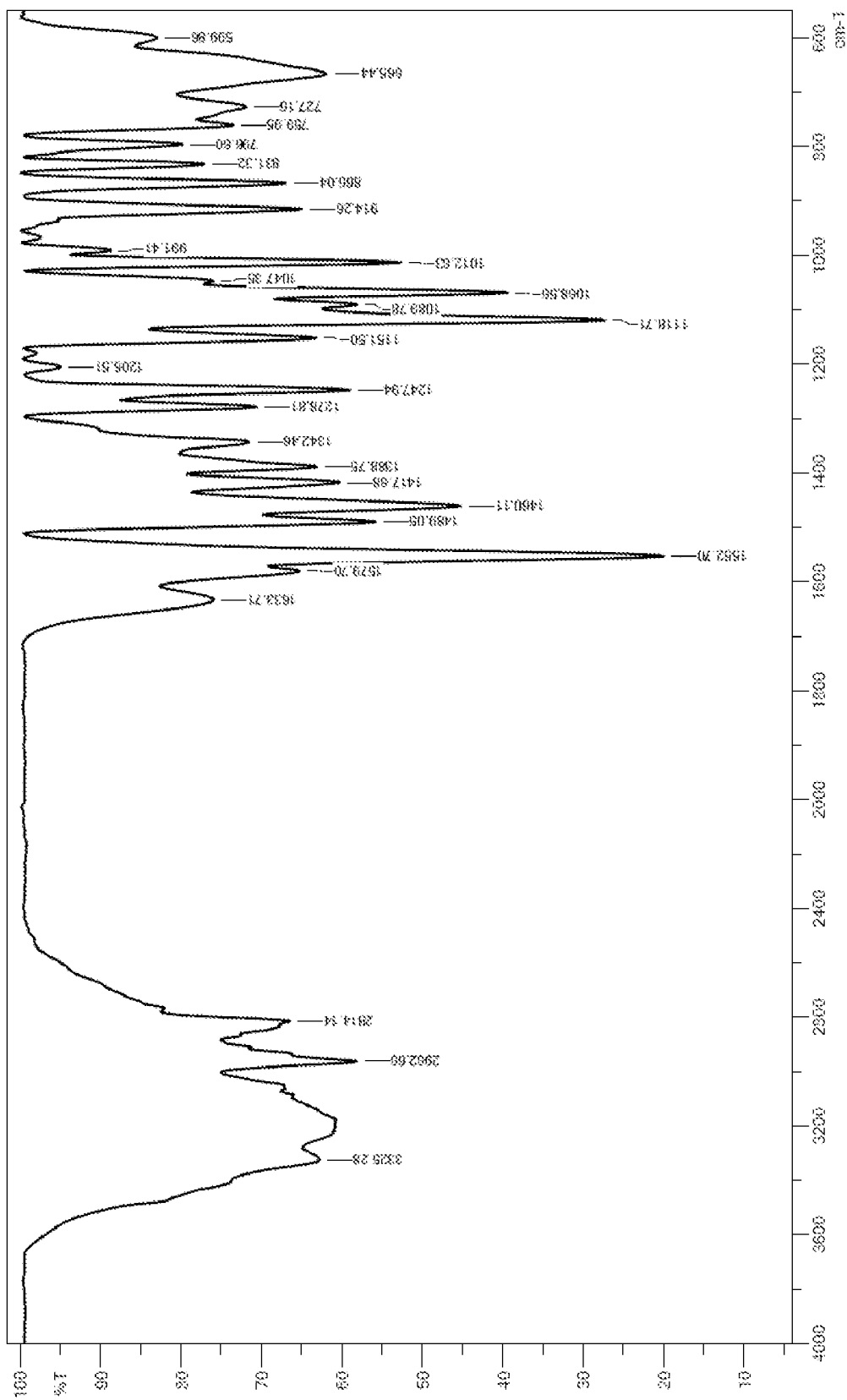
FIG. 16. FT-IR (ATR) spectrum of 5-(4-((2S,5S)-5-(4-chlorobenzyl)-2-methylmorpholino)piperidin-1-yl)-1H-1,2,4-triazol-3-amine hydrated form II obtained in Example 10.

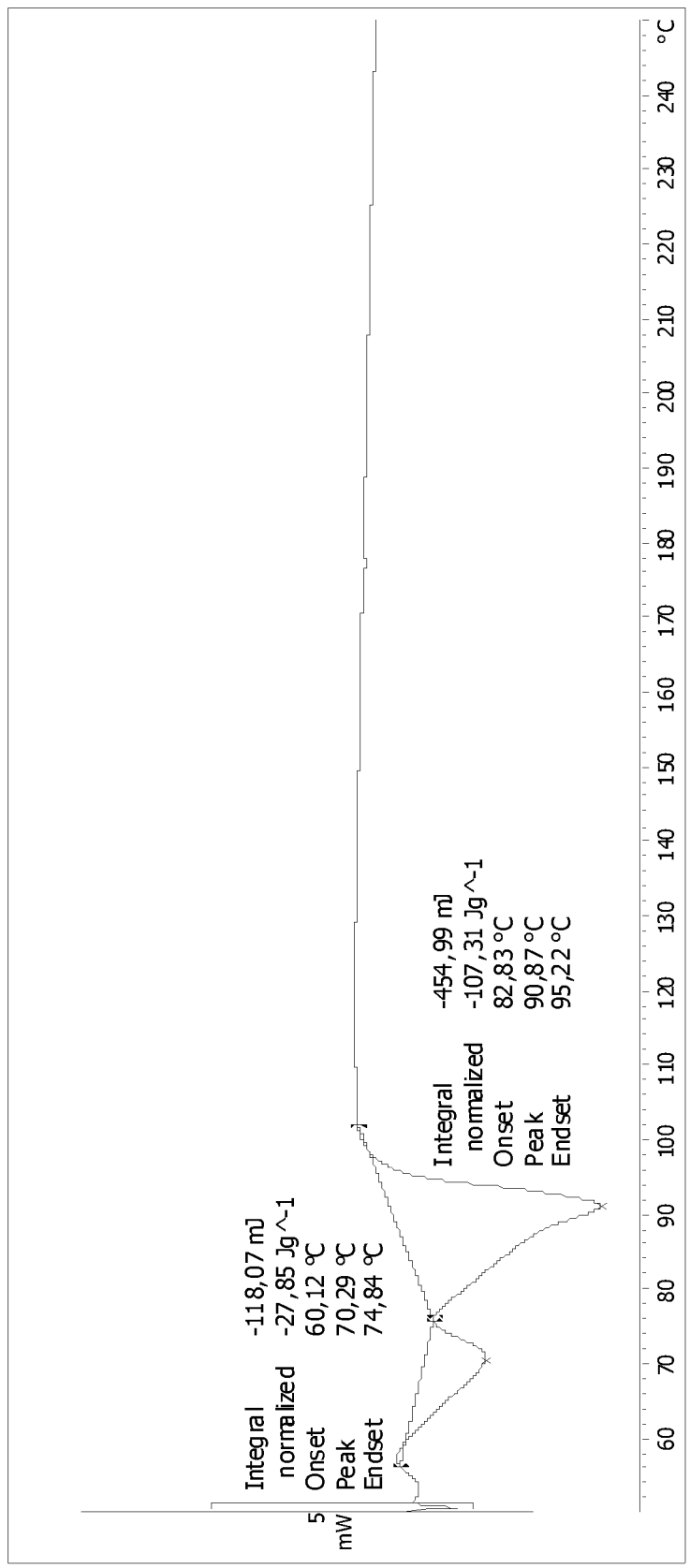
FIG. 17. DSC thermogram of 5-(4-((2S,5S)-5-(4-chlorobenzyl)-2-methylmorpholino)piperidin-1-yl)-1H-1,2,4-triazol-3-amine hydrated form II form obtained in Example 10.

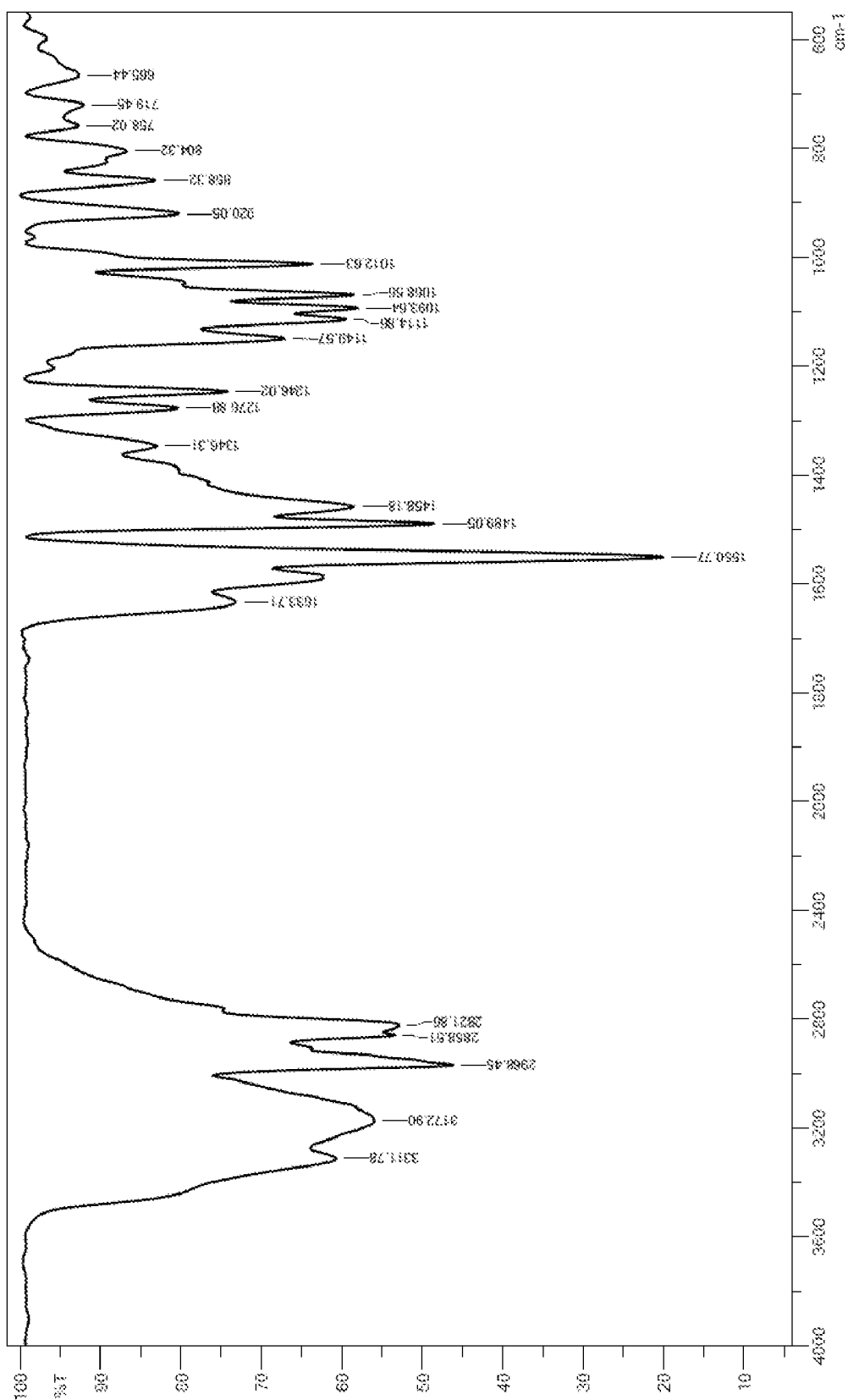
FIG. 18. FT-IR (ATR) spectrum of 5-(4-((2S,5S)-5-(4-chlorobenzyl)-2-methylmorpholino)piperidin-1-yl)-1H-1,2,4-triazol-3-amine amorphous form obtained in Example 11.

PROCESS FOR THE PRODUCTION OF 5-(4-((2S,5S)-5-(4-CHLOROBENZYL)-2-METHYL-MORPHOLINO)PIPERIDIN-1-YL)-1H-1,2,4-TRIAZOL-3-AMINE

RELATED APPLICATIONS

This application claims the benefit of priority to Polish Patent Application number P.431269, filed Sep. 25, 2019; and U.S. Provisional Patent Application Ser. No. 62/905,494, filed Sep. 25, 2019.

FIELD OF INVENTION

The present invention relates to a process for the synthesis of 5-(4-((2S,5S)-5-(4-chlorobenzyl)-2-methylmorpholino)piperidin-1-yl)-1H-1,2,4-triazol-3-amine in two hydrated and one anhydrous crystalline forms. The present invention further relates to methyl (Z)-4-((2S,5S)-5-(4-chlorobenzyl)-2-methylmorpholino)-N-cyanopiperidine-1-carbimidothioate which is an intermediate in this process.

BACKGROUND OF THE INVENTION 5-(4-((2S,5S)-5-(4-Chlorobenzyl)-2-methylmorpholino)piperidin-1-yl)-1H-1,2,4-triazol-3-amine of structural formula 1 has been first described in international patent application WO 2017/037670 (incorporated by reference).

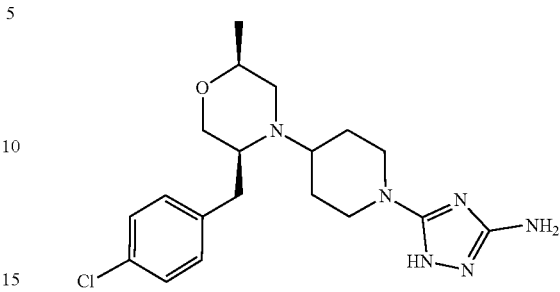

The compound of formula 1 is a dual inhibitor of Acidic Mammal Chitinase (AMCase) and Chitotriosidase 1 (CHIT-1). Such compounds might be used in a treatment of disorders associated with an overexpression of those enzymes. Such disorders are asthma and allergic responses or idiopathic pulmonary fibrosis (IPF) and chronic obstructive pulmonary disease (COPD).

The patent application WO 2017/037670 describes a synthesis of the compound of formula 1 from (2S,5S)-5-(4-chlorobenzyl)-2-methylmorpholine of formula 2. This synthesis is outlined in the scheme below.

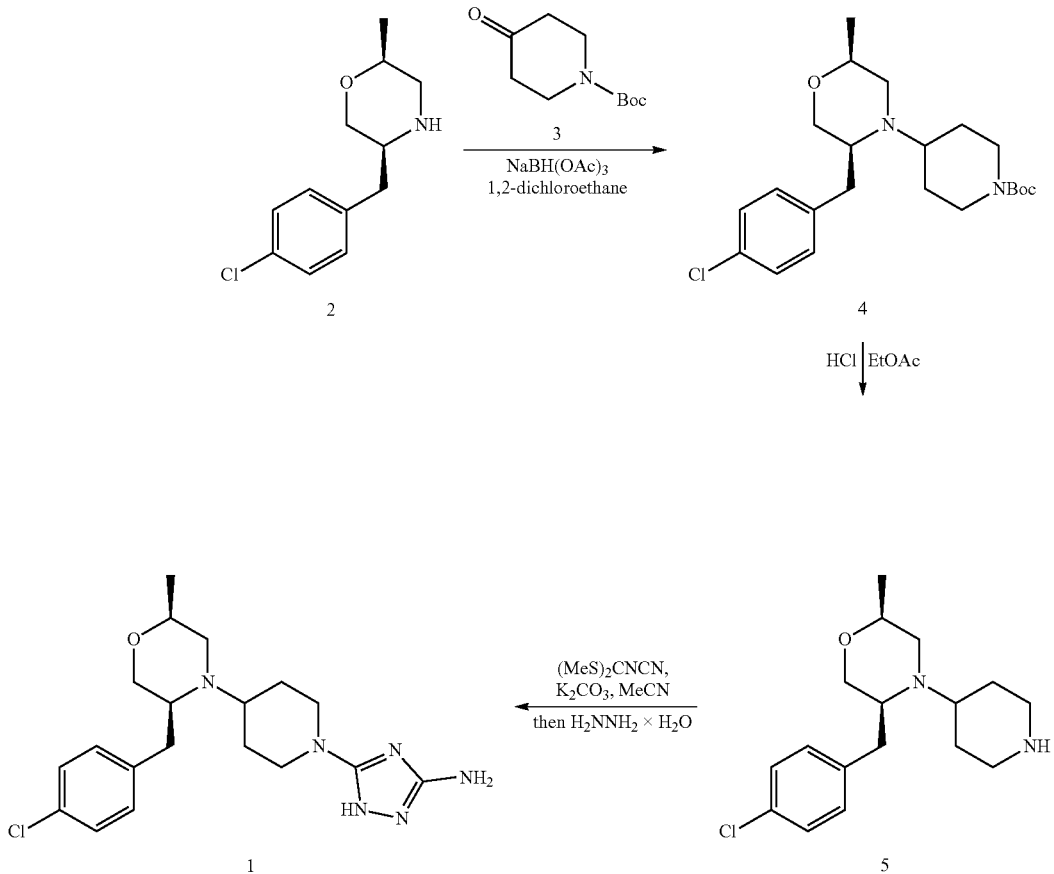

The compound of formula 2 Is reacted with N-(tert-butoxycarbonyl)-4-piperidone of formula 3, sodium triacetoxyborohydride as a reducing agent and glacial acetic acid in 1,2-dichloroethane. After a night crude tert-butyl 4-((2S,5S)-5-(4-chlorobenzyl)-2-methylmorpholino)piperidine-1-carboxylate of formula 4 is isolated by extraction and purified by column chromatography. The pure compound of formula 4 is subjected to a reaction of deprotection of tert-butoxycarbonyl moiety by solution of hydrogen chloride in ethyl acetate resulting in (2S,5S)-5-(4-chlorobenzyl)-2-methyl-4-(piperidin-4-yl)morpholine of formula 5 as a dihydrochloride. In the next step, the compound of formula 5 is reacted with dimethyl N-cyanodithioiminocarbonate in the presence of potassium carbonate as a base in acetonitrile. After few hours of heating, hydrazine monohydrate is added and the reaction mixture is further refluxed for few hours. When the suspension reaches ambient temperature, the solid material is filtered off and the crude product obtained by concentration of the filtrate is purified by column chromatography on silica gel followed by precipitation, yielding the compound of formula 1.

The conversion of the compound of formula 5 into the compound of formula 1 is a sequence of two reactions. In the first step, the compound of formula 5 is converted into an intermediate which is most likely (Z)-4-((2S,5S)-5-(4-chlorobenzyl)-2-methylmorpholino)-N-cyanopiperidine-1-carbimidothioate of formula 6.

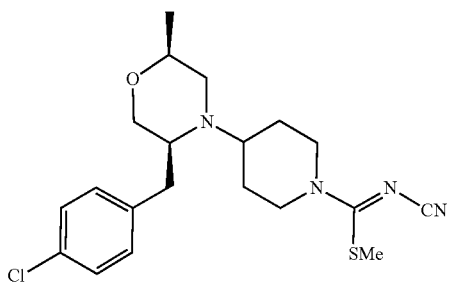

6

The synthesis of the compound of formula 1 as described in the patent application WO 2017/037670 requires two chromatographic purifications, which are cost-ineffective and time consuming. The process involving chromatographic purification rather cannot be considered suitable for industrial scaling up. There is no information if the material obtained in the process is obtained in a crystalline form, which might be considered as stable. Moreover, the Particles Size Distribution is an important parameter of a drug substance, which might have a big impact on the production of drug product in a form of tablets. The patent does not teach if the simple precipitation of the final product as described leads to a material with strictly defined particles size in a repeatable manner. Since the last step of the synthesis presented in WO 2017/037670 requires use of hydrazine, which is known for its carcinogenic properties, the level of the residual hydrazine in the drug substance must be strictly controlled besides of the total purity of the material which is a key factor of every process in the synthesis of a drug substance. According to the features outlined above, there is unmet need for the scalable and efficient process for the synthesis of 5-(4-((2S,5S)-5-(4-chlorobenzyl)-2-methylmorpholino)piperidin-1-yl)-1H-1,2,4-triazol-3-amine of formula 1 which is suitable for the production of a drug product.

SUMMARY OF THE INVENTION

The present invention provides a process for the synthesis of (2S,5S)-5-(4-chlorobenzyl)-2-methyl-4-(piperidin-4-yl)morpholine of formula 5 dihydrochloride hydrate in a solid crystalline state.

The present invention relates to methyl (Z)-4-((2S,5S)-5-(4-chlorobenzyl)-2-methylmorpholino)-N-cyanopiperidine-1-carbimidothioate of formula 6 in a solid crystalline state characterized by at least one of below:
  (i) XRPD peaks at 10.13, 10.98, 12.03, 13.54, 13.98, 14.40, 14.88, 16.84, 18.67, 20.21, 20.85, 21.71, 22.56, 22.98, 24.10, 24.56, 25.27, 27.48, 29.80, 30.43, and 33.36° 2-theta.
  (ii) IR bands at 2959, 2926, 2866, 2820, 2795, 2167, 1541, 1491, 1450, 1431, 1383, 1358, 1273, 1215, 1151, 1117, 1096, 1070, 1043, 1013, 988, 930, 862, 833, 806, 714, 665, and 638 cm$^{-1}$.
  (iii) DSC onset at 156.26° C. and a peak at 157.51° C.

The aforementioned characteristics are substantially in accordance with FIGS. 2 to 4.

The present invention provides a process for the synthesis of methyl (Z)-4-((2S,5S)-5-(4-chlorobenzyl)-2-methylmorpholino)-N-cyanopiperidine-1-carbimidothioate of formula 6 in a solid crystalline state.

The present invention further relates to 5-(4-((2S,5S)-5-(4-chlorobenzyl)-2-methylmorpholino)piperidin-1-yl)-1H-1,2,4-triazol-3-amine of formula 1 hydrated form I in a solid crystalline state characterized by at least one of below:
  (i) XRPD peaks at 6.70, 9.96, 10.68, 12.74, 13.42, 14.20, 14.82, 15.40, 15.58, 16.44, 17.00, 17.46, 18.02, 18.30, 18.64, 19.52, 20.16, 20.66, 21.40, 21.64, 21.86, 22.16, 22.58, 23.22, 23.68, 24.64, 27.00, 27.26, 27.88, and 28.84° 2-theta.
  (ii) IR bands at 3318, 3206, 2963, 2934, 2859, 2833, 1636, 1589, 1553, 1489, 1462, 1404, 1346, 1314, 1277, 1250, 1151, 117, 1092, 1069, 1013, 917, 868, 829, 800, 764, 725, and 673 cm$^{-1}$.
  (iii) DSC onset at 80.60° C. and a peak at 91.32° C.

The aforementioned characteristics are substantially in accordance with FIGS. 7 to 9.

The present invention provides a process for the synthesis of 5-(4-((2S,5S)-5-(4-chlorobenzyl)-2-methylmorpholino)piperidin-1-yl)-1H-1,2,4-triazol-3-amine of formula 1 hydrated form I in a solid crystalline state.

The present invention further relates to 5-(4-((2S,5S)-5-(4-chlorobenzyl)-2-methylmorpholino)-piperidin-1-yl)-1H-1,2,4-triazol-3-amine of formula 1 anhydrous form in a solid crystalline state characterized by at least one of below:
  (i) XRPD peaks at 5.81, 7.39, 9.95, 11.53, 11.97, 12.39, 13.13, 14.07, 14.60, 14.81, 15.11, 16.09, 16.45, 17.15, 17.67, 17.85, 18.21, 18.68, 19.21, 19.84, 20.75, 21.22, 22.24, 23.00, 24.22, 24.98, and 27.48° 2-theta.
  (ii) IR bands at 3252, 3198, 3119, 2955, 2924, 2857, 2793, 1666, 1599, 1543, 1483, 1456, 1404, 1337, 1283, 1248, 1136, 1117, 1094, 1072, 1053, 1013, 908, 858, 795, and 718 cm$^{-1}$.
  (iii) DSC onset at 175.83° C. and a peak at 177.59+ C.

The aforementioned characteristics are substantially in accordance with FIGS. 10 to 12.

The present invention further provides a preparation of 5-(4-((2S,5S)-5-(4-chlorobenzyl)-2-methylmorpholino)piperidin-1-yl)-1H-1,2,4-triazol-3-amine of formula 1 anhydrous form in a solid crystalline state.

The present invention further relates to 5-(4-((2S,5S)-5-(4-chlorobenzyl)-2-methylmorpholino)piperidin-1-yl)-1H-

1,2,4-triazol-3-amine of formula 1 hydrated form II in a solid crystalline state characterized by at least one of below:
(i) XRPD peaks at 10.14, 12.88, 13.50, 13.94, 15.30, 15.48, 16.12, 16.34, 17.60, 17.98, 18.14, 18.64, 18.72, 19.34, 19.76, 20.16, 20.36, 21.64, 22.16, 22.54, 22.86, 23.02, 23.70, 24.28, 25.92, 26.14, 26.32, 27.08, 27.34, 27.70, 30.50, and 39.24° 2-theta.
(ii) IR bands at 3325, 2963, 2814, 1634, 1580, 1553, 1489, 1460, 1418, 1389, 1343, 1279, 1248, 1206, 1151, 1119, 1090, 1069, 1047, 1013, 991, 914, 866, 831, 797, 760, 665, and 600 cm$^{-1}$.
(iii) Two DSC peaks: first with onset at 60.12° C. and a peak at 70.29° C. Second with onset at 82.83° C. and a peak at 90.87° C.

The aforementioned characteristics are substantially in accordance with FIGS. 15 to 17.

The present invention provides a process for the synthesis of 5-(4-((2S,5S)-5-(4-chlorobenzyl)-2-methylmorpholino)piperidin-1-yl)-1H-1,2,4-triazol-3-amine of formula 1 hydrated form II in a solid crystalline state.

The present invention further relates to 5-(4-((2S,5S)-5-(4-chlorobenzyl)-2-methylmorpholino)-piperidin-1-yl)-1H-1,2,4-triazol-3-amine of formula 1 amorphous form in a solid state characterized by:
(i) IR bands at 3312, 3173, 2968, 2859, 2822, 1634, 1551, 1489, 1458, 1346, 1277, 1246, 1150, 1115, 1094, 1069, 1013, 920, 858, 804, 758, 719, and 665 cm$^{-1}$.

The aforementioned characteristic is substantially in accordance with FIG. 18.

The present invention provides a method for the preparation of 5-(4-((2S,5S)-5-(4-chlorobenzyl)-2-methylmorpholino)piperidin-1-yl)-1H-1,2,4-triazol-3-amine of formula 1 amorphous form in a solid state.

The present invention provides industrially scalable methods for the synthesis of the compound of formula 1. The methods avoid chromatographic purifications, which were the most tedious parts of the process. The final product is obtained in a repeatable manner in terms of particle size distribution, purity and the residual hydrazine level, and meets high standards for drug substances.

BRIEF DESCRIPTION OF DRAWINGS

FIG. 1. Scheme of the synthesis of various forms of 5-(4-((2S,5S)-5-(4-chlorobenzyl)-2-methylmorpholino)piperidin-1-yl)-1H-1,2,4-triazol-3-amine.

FIG. 2. XPRD diffractogram of methyl (Z)-4-((2S,5S)-5-(4-chlorobenzyl)-2-methylmorpholino)-N-cyanopiperidine-1-carbimidothioate obtained in Example 3.

FIG. 3. FT-IR (ATR) spectrum of methyl (Z)-4-((2S,5S)-5-(4-chlorobenzyl)-2-methylmorpholino)-N-cyanopiperidine-1-carbimidothioate obtained in Example 3.

FIG. 4. DSC thermogram of methyl (Z)-4-((2S,5S)-5-(4-chlorobenzyl)-2-methylmorpholino)-N-cyanopiperidine-1-carbimidothioate obtained in Example 3.

FIG. 5. $^1$H NMR spectrum (CDCl$_3$ at 400 MHz) of methyl (Z)-4-((2S,5S)-5-(4-chlorobenzyl)-2-methylmorpholino)-N-cyanopiperidine-1-carbimidothioate obtained in Example 3.

FIG. 6. $^{13}$C NMR spectrum (CDCl$_3$ at 100 MHz) of methyl (Z)-4-((2S,5S)-5-(4-chlorobenzyl)-2-methylmorpholino)-N-cyanopiperidine-1-carbimidothioate obtained in Example 3.

FIG. 7. XPRD diffractogram of 5-(4-((2S,5S)-5-(4-chlorobenzyl)-2-methylmorpholino)piperidin-1-yl)-1H-1,2,4-triazol-3-amine hydrated form I calculated from X-ray analysis of a single crystal obtained from a mixture of water and ethanol.

FIG. 8. FT-IR (ATR) spectrum of 5-(4-((2S,5S)-5-(4-chlorobenzyl)-2-methylmorpholino)-piperidin-1-yl)-1H-1,2,4-triazol-3-amine hydrated form I obtained in Example 6.

FIG. 9. DSC thermogram of 5-(4-((2S,5S)-5-(4-chlorobenzyl)-2-methylmorpholino)piperidin-1-yl)-1H-1,2,4-triazol-3-amine hydrated form I obtained in Example 6.

FIG. 10. XPRD diffractogram of 5-(4-((2S,5S)-5-(4-chlorobenzyl)-2-methylmorpholino)-piperidin-1-yl)-1H-1,2,4-triazol-3-amine anhydrous form obtained in Example 8.

FIG. 11. FT-IR (ATR) spectrum of 5-(4-((2S,5S)-5-(4-chlorobenzyl)-2-methylmorpholino)-piperidin-1-yl)-1H-1,2,4-triazol-3-amine anhydrous form obtained in Example 8.

FIG. 12. DSC thermogram of 5-(4-((2S,5S)-5-(4-chlorobenzyl)-2-methylmorpholino)piperidin-1-yl)-1H-1,2,4-triazol-3-amine anhydrous form obtained in Example 8.

FIG. 13. $^1$H NMR (C$_6$D$_6$ at 700 MHz) spectrum of 5-(4-((2S,5S)-5-(4-chlorobenzyl)-2-methyl-morpho-lino)piperidin-1-yl)-1H-1,2,4-triazol-3-amine anhydrous form obtained in Example 8.

FIG. 14. $^{13}$C NMR (C$_6$D$_6$ at 176 MHz) spectrum of 5-(4-((2S,5S)-5-(4-chlorobenzyl)-2-methylmorpholino)piperidin-1-yl)-1H-1,2,4-triazol-3-amine anhydrous form obtained in Example 8.

FIG. 15. XPRD diffractogram of 5-(4-((2S,5S)-5-(4-chlorobenzyl)-2-methylmorpholino)-piperidin-1-yl)-1H-1,2,4-triazol-3-amine hydrated form II calculated from X-ray analysis of a single crystal obtained from a mixture of water and methanol.

FIG. 16. FT-IR (ATR) spectrum of 5-(4-((2S,5S)-5-(4-chlorobenzyl)-2-methylmorpholino)-piperidin-1-yl)-1H-1,2,4-triazol-3-amine hydrated form II obtained in Example 10.

FIG. 17. DSC thermogram of 5-(4-((2S,5S)-5-(4-chlorobenzyl)-2-methylmorpholino)piperidin-1-yl)-1H-1,2,4-triazol-3-amine hydrated form II form obtained in Example 10.

FIG. 18. FT-IR (ATR) spectrum of 5-(4-((2S,5S)-5-(4-chlorobenzyl)-2-methylmorpholino)-piperidin-1-yl)-1H-1,2,4-triazol-3-amine amorphous form obtained in Example 11.

DETAILED DESCRIPTION OF THE INVENTION

The present invention provides the efficient and scalable process for the synthesis of (2S,5S)-5-(4-chlorobenzyl)-2-methyl-4-(piperidin-4-yl)morpholine of formula 5. Compared to the description of the original approach outlined in the "Background of the Invention", various changes were introduced into the procedure in order to improve yield and simplify the synthesis, making it scalable. The compound of formula 2 is reacted with N-(tert-butoxycarbonyl)-4-piperidone of formula 3, in the presence of a reducing agent, sodium cyanoborohydride and an additive, preferably zinc chloride in a solvent, preferably an alcohol, more preferably in methanol, at a temperature from 0° C. to reflux, preferably at ambient temperature. When full conversion of the starting material is obtained, tert-butyl 4-((2S,5S)-5-(4-chlorobenzyl)-2-methylmorpholino)piperidine-1-carboxylate of formula 4 is isolated by extraction and the crude product is dissolved in a solvent, preferably ethyl acetate, and a solution of hydrochloric acid, preferably concentrated hydrochloric acid, is added. When full conversion of the starting material is obtained, the solvent is swapped to a polar solvent, preferably to methanol. To the solution a solvent, preferably acetone, is added and the solution is allowed to cool down to ambient temperature. The product crystallizes upon cooling and the crystals are filtered off. The filter cake is rinsed with a solvent, preferably acetone, and dried in the air to afford (2S,5S)-5-(4-chlorobenzyl)-2-methyl-4-(piperidin-4-yl)morpholine of formula 5 as white crystals. Careful analysis of the obtained material showed that the product was obtained as dihydrochloride hydrate.

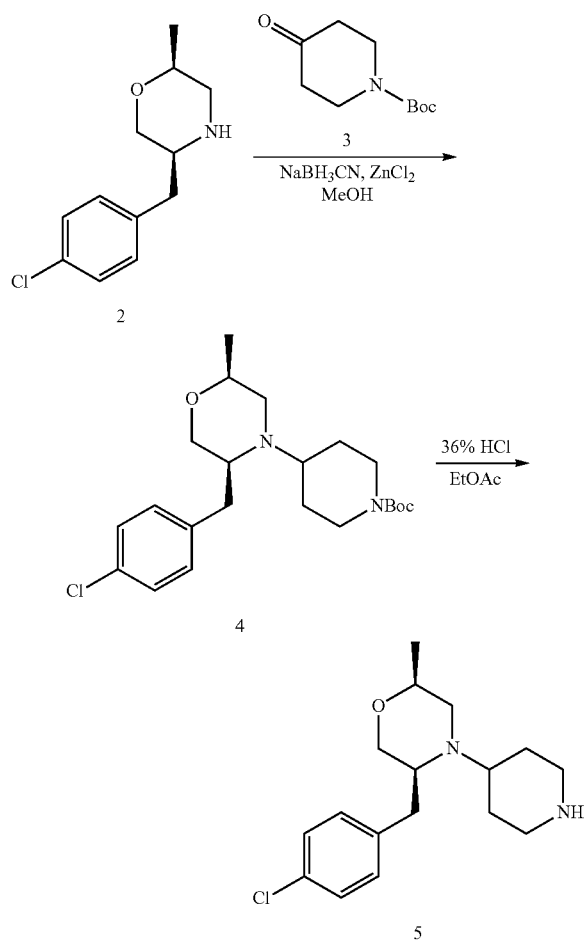

A crucial step in the synthesis of the compound formula 2 is the reaction of a mixture of the compounds of formula 7 and 8 with potassium tert-butoxide leading to an amide of formula 9. Only the compound of formula 8 cyclizes into the compound of formula 9. In the reaction conditions, the compound of formula 7 epimerizes into the compound of formula 8 which cyclizes into the compound of formula 9. Due to that fact, the reaction of potassium tert-butoxide with the mixture of the compounds of formula 7 and 8 provides exclusively the compound of formula 9. The compound of formula 9 epimerizes in the reaction conditions to a compound of formula 10 which is a by-product of the reaction. The crude product of formula 9 is then crystallized but complete removal of the unwanted compound of formula 10 is tedious and leads to significant loss of the product. Reduction of the compound of formula 9 leads to the compound of formula 2, but when the compound of formula 9 is contaminated with the compound of the formula 10, then the compound of formula 2 contains the compound of formula 11 obtained as the product of reduction of the compound of formula 10.

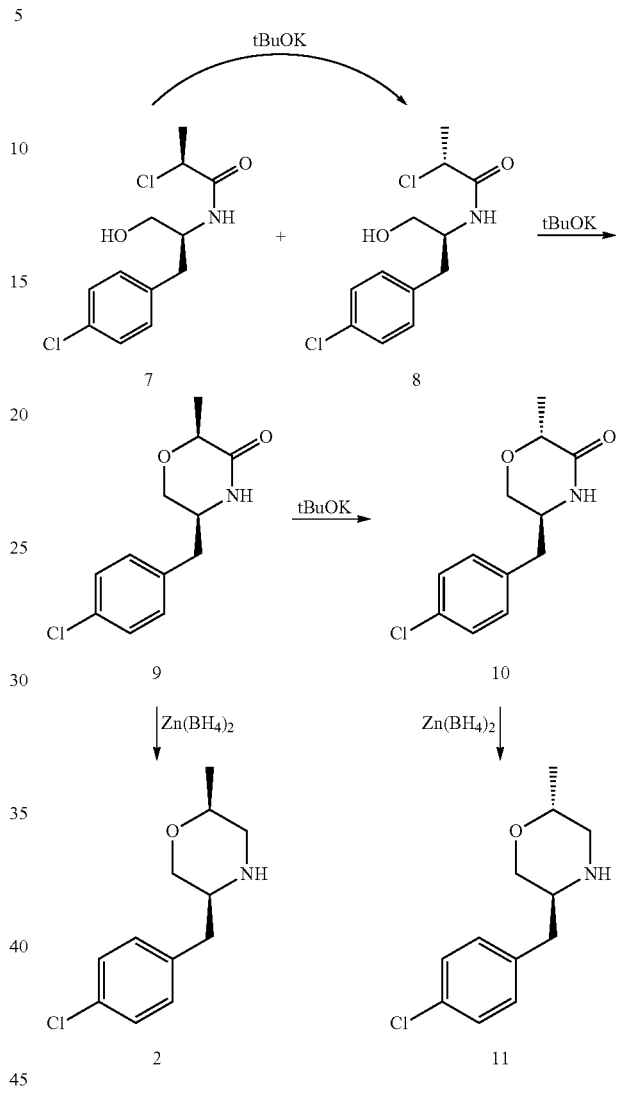

Under conditions described in the patent application WO 2017/037670 (sodium triacetoxyborohydride, acetic acid and 1,2-dichloroethane), the compound of formula 11 reacts with N-Boc-4-piperidinone leading to a by-product of formula 12 which is observed in crude compound of formula 3. The impurity of formula 12 can be removed by the careful purification on silica gel but such an approach is unacceptable on a kilo-scale. The compound of formula 11 does not react with N-Boc-4-piperidinone when conditions described in this patent application (sodium cyanoborohydride, zinc chloride and methanol) are used. Since the compound of formula 11 can be easily removed by crystallization after removal of the tert-butoxycarbonyl protection group, the present invention relates to a method for the synthesis of the compound of formula 5 with no impurity of formula 13. Moreover, the conditions described in this application unobviously allow one to use hydrochloride salt of the compound of formula 2 as the starting material which can facilitate the process. The compound of formula 2 is an oil of limited stability, what means that it must be kept in a form of salt in order to prevent decomposition. To the contrary, the reaction described in WO 2017/037670 is not proceeding when hydrochloride of the compound of formula 2 is used as the starting material and the salt must be first converted into the free base which is an additional operation.

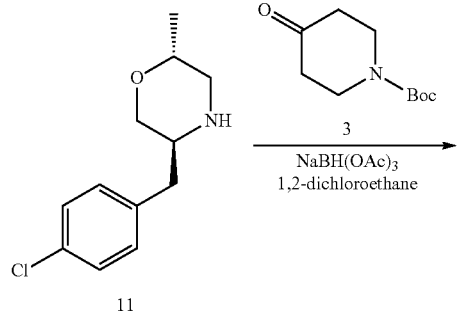

11

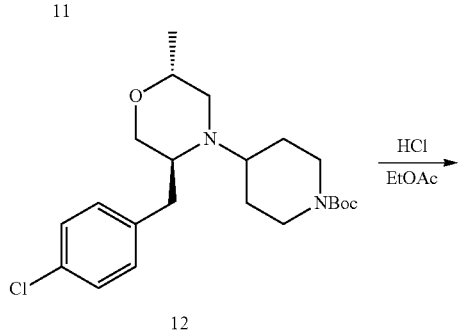

12

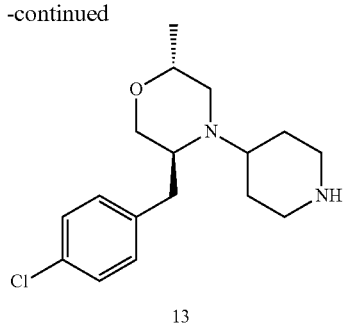

13

The present invention further provides a method for the synthesis of methyl (Z)-4-((2S,5S)-5-(4-chlorobenzyl)-2-methylmorpholino)-N-cyanopiperidine-1-carbimidothioate of formula 6. This compound was never isolated nor described yet. The related compound can be synthetized by the reaction of (2S,5S)-5-(4-chlorobenzyl)-2-methyl-4-(piperidin-4-yl)morpholine of formula 5 with dimethyl N-cyanodithioiminocarbonate in the presence of a base, preferably trialkylamine, more preferably triethylamine, in a solvent, preferably ethanol, 1-propanol or 2-propanol. The reaction is carried out at a temperature from room temperature to reflux, preferably at 50° C. The reaction mixture is allowed to cool down to ambient temperature when full conversion of the starting material is obtained. The product crystallizes upon cooling. The material is filtered off and the filter cake is washed with the solvent, preferably ethanol, 1-propanol, or 2-propanol, and dried to afford the compound of formula 6.

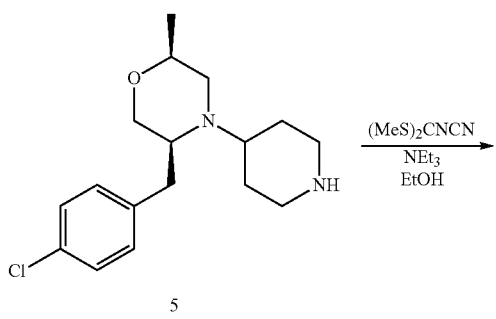

5

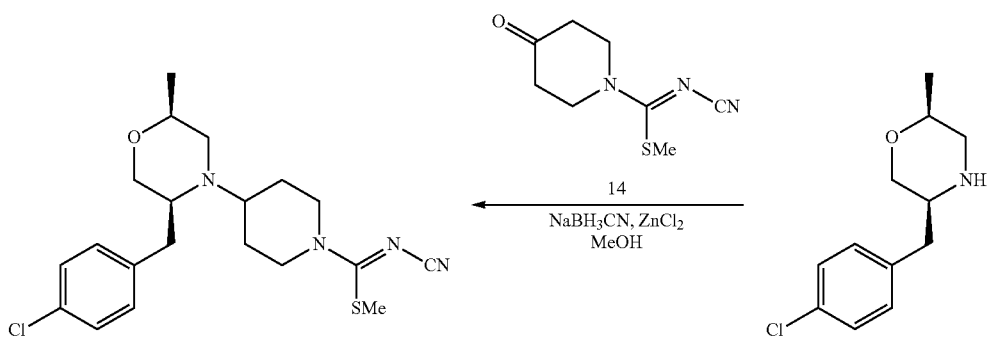

6 2

The present invention further provides a method for the synthesis of the compound of formula 6 directly from the compound of formula 2 avoiding the three-step synthesis. This approach relates to the reaction of the compound of formula 2 with 4-oxopiperidine methyl N-cyanothioimidocarbamate of formula 14. The compound of formula 14 can be easily obtained from commercially available 4,4-dihydroxypiperidine hydrochloride by a reaction with dimethyl N-cyanodithioiminocarbonate in the presence of a base, preferably trialkylamine, more preferably triethylamine, in a solvent, preferably in a mixture of solvents, and more preferably in a mixture of 2-propanol and water, at a temperature from 0° C. to reflux, preferably at ambient temperature. The reaction mixture is quenched with 6 M solution of hydrochloric acid and extracted with organic solvent, preferably dichloromethane. The solution is washed with water and the solvent is swapped to a polar solvent, preferably 2-propanol. To the hot solution, a non-polar solvent, preferably isopropyl ether, is added, leading to crystallization of the product. The solid is filtered off and the filter cake is rinsed with a solvent, preferably with a mixture of solvents, and more preferably with a mixture of 2-propanol and isopropyl ether, and then dried to afford the compound of formula 14 as an off-white solid.

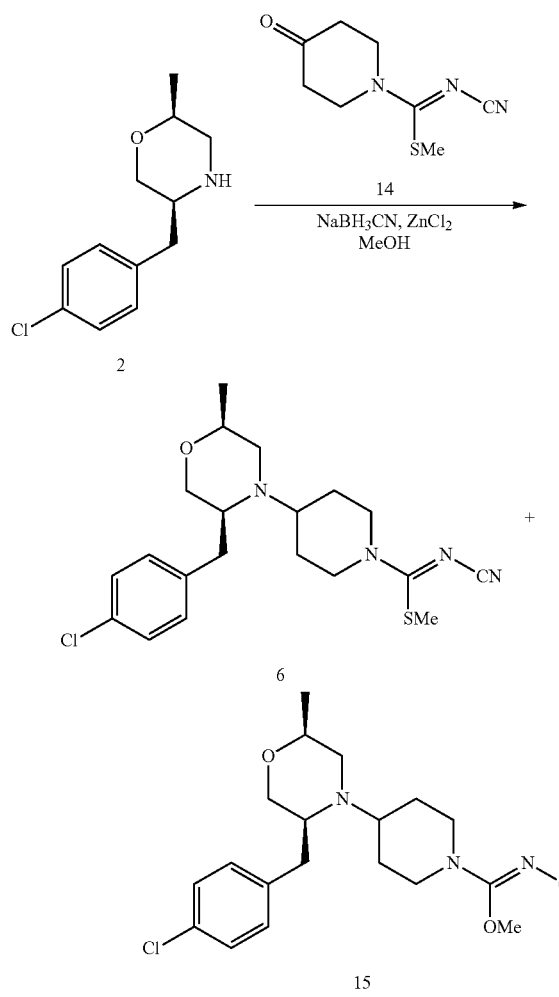

The reaction between the compound of formula 2 and the compound of formula 14 carried out in the conditions described in WO 217/037670 for the synthesis the compound of the formula 4 did not proceed after simple replacing the ketone compound of formula 3 with the ketone compound of formula 14. Moreover, the conditions for the synthesis of the compound of formula 4 from the compound of formula 2, as described in this application, led to a mixture of the compound of formula 6 and a by-product of formula 15, after simple replacing the compound of formula 3 with the compound of formula 14. This gave rise to an unmet need to develop new conditions for the synthesis of the compound of formula 6 directly from the compound of the formula 2.

The reaction between the compound of formula 2 and the compound of formula 14 is carried out in the presence of a reducing agent, preferably sodium cyanoborohydride, and an additive, preferably zinc chloride, in a polar solvent, preferably ethanol, at a temperature from 0° C. to reflux, preferably at ambient temperature. After full conversion of the starting material is obtained, the reaction mixture is quenched with a 1 M solution of sodium hydroxide and extracted with organic solvent, preferably dichloromethane. The solvent is swapped to organic solvent, preferably ethanol. The solution is allowed to cool down to ambient temperature, leading to crystallization of the product. The solid is filtered off and the filter cake is rinsed with a solvent, preferably with ethanol, and dried to afford the compound of formula 6 as a white solid.

The target molecule of formula 1 can be obtained either from the compound of formula 5 or the compound of formula 6. Moreover, this patent application describes methods for the preparation of an anhydrous form, two hydrated forms (hydrated forms I and II) and an amorphous form of the target molecule of formula 1. The methods outlined in this paragraph are summarized in FIG. 1.

The present invention further provides a method for the synthesis of the compound of formula 1 hydrated form I from the compound of formula 5 (reaction A in FIG. 1). The compound of formula 5 is suspended in a solvent, preferably in ethanol, and dimethyl N-cyanodithioiminocarbonate is added, followed by a base, preferably trialkylamine, more preferably triethylamine, at a temperature from ambient temperature to boiling point, preferably at 40° C. When full conversion of the starting material is achieved, hydrazine monohydrate is added, the reaction is continued at a temperature from ambient temperature to boiling point, preferably at 60° C. When full conversion of the intermediate is achieved, water is added, and the solution is cooled down to a temperature from −20° C. to ambient temperature, preferably to 5° C. The precipitated solid is filtered off and the filter cake is rinsed with a mixture of water and an organic solvent, preferably ethanol, and dried to afford the compound of formula 1 hydrated form I as a white solid.

The present invention further provides method for the synthesis of the compound of formula 1 hydrated form I from the compound of formula 6 (reaction B in FIG. 1). The compound of formula 6 is suspended in a solvent, preferably in ethanol, at a temperature from ambient temperature to boiling point, preferably at 60° C., and hydrazine monohydrate is added. When full conversion of the starting material is achieved, water is added and the solution is cooled down to a temperature from −20° C. to ambient temperature, preferably to 5° C. The precipitated solid is filtered off and the filter cake is rinsed with a mixture of water and an organic solvent, preferably ethanol, and dried to afford the compound of formula 1 hydrated form I as a white solid.

The present invention further provides a method for the synthesis of the compound of formula 1 anhydrous form from the compound of formula 6 (reaction C in FIG. 1). The reaction of the compound of formula 6 with hydrazine monohydrate is carried out in an organic solvent, preferably acetonitrile, at a temperature from ambient temperature to boiling point, preferably at 60° C. When full conversion of the starting material is achieved, the solution is allowed to cool down to ambient temperature and the product precipitates upon cooling. The solid is filtered off and the filter cake is rinsed with a solvent, preferably with acetonitrile, and dried to afford the compound of formula 1 anhydrous form as a white solid.

Compared to WO 2017/037670, when the compound of the formula 1 was obtained in a one-pot approach, the process employing separation of the compound of the formula 6 unobviously allows to obtain the compound of the formula 1 anhydrous form in higher yield (86% in this application versus 72% in WO 2017/037670). The crucial factor of the second step involving reaction of the compound of formula 6 is acetonitrile used as the solvent. In more polar solvents (i.e., methanol, ethanol or 2-propanol), yield of the reaction is much lower. On the other hand, when less polar solvents (i.e., dichloromethane, methyl tert-butyl ether or toluene) are applied, the level of residual hydrazine becomes unacceptable.

The present invention further provides a method for the preparation of the anhydrous form of the compound of formula 1 from its hydrated form I (method D in FIG. 1). The compound of formula 1 in hydrated form I is suspended in an organic solvent, preferably in ethyl acetate, and the suspension is heated up to reflux. Upon heating the suspension turns into a clear solution. The solution is distilled until the temperature of volatiles reaches 76° C. During distillation the product precipitates. The solid is filtered off at ambient temperature. The filter cake is rinsed with an organic solvent, preferably ethyl acetate, and dried to afford the compound of formula 1 in the anhydrous form as white crystals.

The synthesis of the compound of formula 1 hydrated form I followed by the synthesis of the compound of the formula 1 anhydrous form has a significant advantage as compared to the synthesis of the compound of formula 1 described in WO 2017/037670. Under new conditions, the precipitation of the compound of the formula 1 hydrated form I unobviously allows to control the amount of residual hydrazine which is considered as a genotoxic impurity and must be controlled at ppm levels. The method outlined in the previous paragraph was used for the synthesis of three batches of the anhydrous form of the compound of formula 1. This material was carefully analyzed for purity, residual hydrazine level and particle size distribution.

| Purity by HPLC | Residual hydrazine level | Particle size distribution |
| --- | --- | --- |
| 99.92% | 0.3 ppm | D10 152 μm, D50 255 μm, D90 403 μm |
| ≥99.95% | 0.1 ppm | D10 202 μm, D50 357 μm, D90 577 μm |
| ≥99.95% | 0.2 ppm | D10 154 μm, D50 284 μm, D90 485 μm |

The present invention further provides a method for the preparation of the hydrated form II of the compound of formula 1 from its anhydrous form (method E in FIG. 1). The compound of the formula 1 anhydrous form is dissolved in methanol at reflux. To the solution water is added and product precipitates. The suspension is allowed to cool down to a temperature from −20° C. to ambient temperature, preferably to 5° C. The solid as aged and filtered off. The filter cake is rinsed with a mixture of water and methanol, and dried to afford the compound of formula 1 hydrated form II as a white solid.

Due to the fact that the compound of formula 6 is not stable in methanol, it is not possible to obtain the hydrated form II directly from the compound 6 as for hydrated form I of the compound of formula 1. Both hydrated forms I and II of the compound of formula 1 are unstable, leading to amorphous form upon drying. The XPRD data for the dried material and data calculated from X-ray structure differ. Moreover, analysis of a dried single crystal of the compound of formula 1 hydrated form I used from structure determination showed lack of crystalline structure which leads to a conclusion that crystal structure collapses upon drying. The amorphous form of the compound of formula 1 can be prepared in a more convenient way by melting the anhydrous form or hydrated form I or II of the compound of formula 1 followed by cooling off the material to ambient temperature. After grinding the glass-like solid, anhydrous form of the compound of formula 1 is an off-white solid.

EXAMPLES

The invention will be illustrated by the following examples.

The following examples are provided for illustrative purposes only and are not intended to limit the scope of the invention in any way.

General Procedures

All solvents, substrates and reagents that were commercially available were used without further purification.

NMR spectra were recorded on Agilent Mercury 400 MHz spectrometer and Bruker Avance 500, and 700 MHz spectrometers (DXR500, and DXR700, respectively).

NMR spectra were recorded in the indicated deuterated solvents that were commercially available.

Resonances are given in parts per million relative to tetramethylsilane (δ 0.00 ppm for $CD_3Cl$) or residual solvent (δ 4.87 ppm for $CD_3OD$ or δ 7.61 ppm for $C_6D_6$) for $^1H$ NMR, or to solvent (δ 49.00 ppm for $CD_3OD$, δ 77.26 ppm for $CDCl_3$ or δ 128.06 ppm for $C_6D_6$) for $^{13}C$ NMR). Data are reported as follows: chemical shift (δ), multiplicity (s=singlet, d=doublet, t=triplet, m=multiplet, bs=broad singlet), coupling constants (J in Hz) and integration.

FT-IR spectra were recorded with Shimadzu IRTracer-100 in ATR mode (zinc selenide crystal).

X-ray diffraction experiments at T=100(2) K were performed on good-quality single crystals. The crystals were mounted with Paratone-N oil to the MiTeGen micromount. Diffraction data were collected on the Agilent Technologies SuperNova Dual Source with the CuKα radiation (λ=1.54184 Å). The lattice parameters were obtained by least-squares fit to the optimized setting angles of the reflections collected by using the CrysAlis CCD software. Data were reduced using the CrysAlis RED program. The multi-scan empirical absorption correction using spherical harmonics, implemented in SCALE3 ABSPACK scaling algorithm, was applied. The structural determination procedure was carried out using the SHELX package.

XPRD diffractograms of compounds obtained in Examples 3 and 8 were recorded with Bruker D8 Discover powder X-ray diffractometer equipped with Cu CuKα radiation (1.54 Å) and Vantec detector. The samples were analyzed in a continuous mode with step size of 0.01222276° and step time of 0.9 s over an angular range of 3-50° 2θ. XPRD diffractograms of compounds obtained in Examples 6 and 10 were calculated from single-crystal X-ray data using Mercury software.

DSC thermograms were recorded with Mettler Toledo DSC 3 at 5° C./min. gradient.

PSD data were recoded with Malvern Mastersizer 2000 in Isopar G.

The purity was measured by HPLC-UV method. The analysis is performed on Phenyl-Hexyl analytical column (Kinetex Phenyl-Hexyl, 2.1 mm×100 mm; 2.6 μm) at 20° C., and at mobile phase flow rate of 0.3 mL/min. The mobile phase is a mixture of solvent A (900 mL water, 100 mL methanol, 1 g ammonium formate) and solvent B (100 mL water, 900 mL methanol, 1 g ammonium formate). Elution is carried out under gradient elution (60% of solvent B from 0.0 to 2.0 min then from 60% to 85% of solvent B from 2.0 to 2.5 min then 85% of solvent B from 2.5 to 5.5 min then from 85% to 100% of solvent B from 5.5 to 6.0 min then 100% of solvent B from 6.0 to 8.0 min then from 100% to 60% of solvent B from 8.0 to 8.2 min then at 60% of solvent B from 8.2 to 13.0 min). Peaks are recorded using UV detection at 225 nm.

The residual level of hydrazine was measured by HPLC-UV method. A sample is prepared by dissolution of 75 mg in 1 mL of methanol. 1 mL of 1 M HCl solution is added followed by 1 mL of benzaldehyde solution (0.6 g/mL in methanol/water 1/1 (v/v)) and the solution is vortexed. 1 mL of n-heptane is added and the biphasic system is vortexed and centrifuged at high speed. The upper phase (5 μL) is injected for analysis. Chromatographic (HPLC-UV) analysis is performed on C18 analytical column (LumiSep C18, 2.1 mm×50 mm; 3 μm) maintained at 40° C., and mobile phase flow rate of 0.5 mL/min. The mobile phase is composed of a mixture of solvent A (900 mL water, 100 mL acetonitrile, 1 g ammonium formate) and solvent B (100 mL water, 900 mL acetonitrile, 1 g ammonium formate). Elution is carried out under isocratic conditions (55% of solvent B until completion of the run at 6 min.) Peaks are recorded using UV detection at 305 nm. Benzaldehyde hydrazone retention time is ca. 2.43 min.

Boc denotes tert-butoxycarbonyl protecting group.

Reaction yields are expressed by mole %.

HPLC purities are expressed by area-under-the-curve %.

Content of water by Karl Fischer method and loss on drying are expressed by weight %.

Example 1

Preparation of (2S,5S)-5-(4-chlorobenzyl)-2-methyl-4-(piperidin-4-yl)morpholine dihydrochloride hydrate (5, dihydrochloride hydrate) from (2S,5S)-5-(4-chlorobenzyl)-2-methylmorpholine (2)

(2S,5S)-5-(4-Chlorobenzyl)-2-methylmorpholine (2, 13.06 g), N-Boc-4-piperidinone (3, 17.30 g) and zinc chloride (7.89 g) were dissolved in methanol (130 ml). Sodium cyanoborohydride (5.45 g) was added portionwise and the reaction was stirred overnight. The reaction mixture was partitioned between ethyl acetate (240 mL) and 1 M sodium hydroxide solution (240 ml). The aqueous layer was extracted with ethyl acetate (240 ml), and the combined extracts were washed with half-saturated sodium chloride solution (240 mL), and dried. The solution was concentrated to ca. 200 mL and concentrated hydrochloric add (40 mL) was added. After half an hour water was distilled off using a Dean-Stark trap. Ethyl acetate was swapped for methanol and concentrated to ca. 100 mL of volume. To the solution, acetone (300 mL) was slowly added leading to precipitation of the product. The suspension was allowed to cool down to ambient temperature and aged for an hour. The solid was filtered off and the filter cake was rinsed with acetone (2×100 mL) and dried in the air to afford (2S,5S)-5-(4-chlorobenzyl)-2-methyl-4-(piperidin-4-yl)morpholine dihydrochloride hydrate (5, dihydrochloride hydrate, 20.92 g, 90% yield over two steps, 99.5% purity by HPLC) as a white solid.

$^1$H NMR (500 MHz, CD$_3$OD) δ 7.40-7.30 (m, 4H), 4.08-3.98 (m, 1H), 3.96-3.83 (m, 2H), 3.82-3.74 (m, 1H), 3.69 (d, J=13.3 Hz, 1H), 3.67-3.54 (m, 3H), 3.29-3.06 (m, 5H), 2.60-2.50 (m, 2H), 2.26-2.11 (m, 2H), and 1.32 (d, J=6.2 Hz, 3H) ppm.

$^{13}$C NMR (125 MHz, CD$_3$OD) δ 135.2, 134.4, 132.5, 130.1, 71.7, 65.7, 58.0, 57.6, 50.4, 43.7, 43.5, 28.4, 25.2, 25.0, and 18.7 ppm.

Example 2

Preparation of (2S,5S)-5-(4-chlorobenzyl)-2-methyl-4-(piperidin-4-yl)morpholine dihydrochloride hydrate (5, dihydrochloride hydrate) from (2S,5S)-5-(4-chlorobenzyl)-2-methylmorpholine hydrochloride (2, hydrochloride)

(2S,5S)-5-(4-Chlorobenzyl)-2-methylmorpholine (2, hydrochloride, 9.99 g), N-Boc-4-piperidinone (3, 11.39 g) and zinc chloride (5.23 g) were dissolved in methanol (80 mL). Sodium cyanoborohydride (3.71 g) was added portionwise and the reaction was stirred overnight. The reaction mixture was partitioned between ethyl acetate (240 mL) and 1 M sodium hydroxide solution (240 ml). The aqueous layer was extracted with ethyl acetate (240 ml), and the combined extracts were washed with half-saturated sodium chloride solution (240 ml), and dried. The solution was concentrated to dryness and the residue was dissolved in 3 M hydrochloric acid solution in ethyl acetate. After an hour the solution was concentrated to dryness and dissolved in MeOH (30 mL) at reflux. To the clear solution acetone (30 mL) was added and the mixture was allowed to cool down to ambient temperature to precipitate the product. To the suspension, a second portion of acetone (20 mL) was added and the suspension was aged for an hour. The solid was filtered off and the filter cake was rinsed with acetone (2×30 mL) and dried in the air to afford (2S,5S)-5-(4-chlorobenzyl)-2-methyl-4-(piperidin-4-yl)morpholine dihydrochloride hydrate (5, dihydrochloride hydrate, 12.51 g, 86%% yield over two steps, 98.9% purity by HPLC) as a white solid.

$^1$H NMR (500 MHz, CD$_3$OD) δ 7.40-7.30 (m, 4H), 4.08-3.98 (m, 1H), 3.96-3.83 (m, 2H), 3.82-3.74 (m, 1H), 3.69 (d, J=13.3 Hz, 1H), 3.67-3.54 (m, 3H), 3.29-3.06 (m, 5H), 2.60-2.50 (m, 2H), 2.26-2.11 (m, 2H), and 1.32 (d, J=6.2 Hz, 3H) ppm.

$^{13}$C NMR (125 MHz, CD$_3$OD) δ 135.2, 134.4, 132.5, 130.1, 71.7, 65.7, 58.0, 57.6, 50.4, 43.7, 43.5, 28.4, 25.2, 25.0, and 18.7 ppm.

Example 3

Preparation of methyl (2)-4-((2S,5S)-5-(4-chlorobenzyl)-2-methylmorpholino)-N-cyano-piperidine-1-carbimidothioate (6) from (2S,5S)-5-(4-chlorobenzyl)-2-methyl-4-(piperidin-4-yl)morpholine dihydrochloride hydrate (5, dihydrochloride hydrate)

(2S,5S)-5-(4-Chlorobenzyl)-2-methyl-4-(piperidin-4-yl) morpholine dihydrochloride hydrate (5, dihydrochloride hydrate, 5.82 g) and dimethyl N-cyanodithioiminocarbonate (2.34 g) were suspended in ethanol (60 mL). To the suspension, triethylamine (6.1 mL) was added and the reaction mixture was heated up to 40° C. The suspension turned into a clear solution upon heating. After 3 h, the solution was allowed to cool down to ambient temperature and the product precipitated. The suspension was aged and the solid was filtered off. The filter cake was rinsed with ethanol (5 mL) and dried to afford methyl (Z)-4-((2S,5S)-5-(4-chlorobenzyl)-2-methylmorpholino)-N-cyanopiperidine-1-carbimidothioate (6, 5.48 g, 92% yield, 99.2% purity by HPLC) as a white fluffy solid.

$^1$H NMR (400 MHz, CDCl$_3$) δ 7.28-7.22 (m, 2H), 7.13-7.08 (m, 2H), 4.45-4.34 (m, 2H), 3.68-3.54 (m, 2H), 3.46 (dd, J=11.5, 2.7 Hz, 1H), 3.32 (dd, J=12.1, 2.8 Hz, 2H), 3.01 (dd, J=12.9, 10.8 Hz, 1H), 2.88-2.77 (m, 2H), 2.76 (s, 3H), 2.71-2.62 (m, 2H), 2.36 (dd, J=11.8, 10.3 Hz, 1H), 2.07-1.94 (m, 2H), 1.68-1.47 (m, 2H), and 1.21 (d, J=6.2 Hz, 3H) ppm.

$^{13}$C NMR (100 MHz, CDCl$_3$) δ 168.7, 138.3, 132.0, 130.8, 128.8, 115.4, 72.5, 67.8, 55.8, 55.4, 50.0, 46.9, 30.3, 29.8, 27.5, 19.3, and 16.4 ppm.

FT-IR (ATR): 2959, 2926, 2866, 2820, 2795, 2167, 1541, 1491, 1450, 1431, 1383, 1358, 1273, 1215, 1151, 1117, 1096, 1070, 1043, 1013, 988, 930, 862, 833, 806, 714, 665, and 638 cm$^{-1}$.

Example 4

Preparation of 4-oxopiperidine methyl N-cyanothioimidocarbamate (14)

Dimethyl N-cyanodithioiminocarbonate (15.02 g) and 4,4-dihydroxypiperidine hydrochloride (19.72 g) were dissolved in a mixture of 2-propanol (60 mL) and water (90 mL). To the solution, triethylamine (17.3 mL) was added. After 2 h the reaction was quenched with 6 M solution of hydrochloric add (30 mL) and extracted with CH$_2$Cl$_2$ (4×75 ml). The combined organic layers were washed with water (75 ml), and 2-propanol (90 mL) was added. The solution was concentrated under atmospheric pressure to volume of 90 mL, then to the boiling solution isopropyl ether (90 mL) was added portionwise, maintaining the reflux. The product precipitated and the suspension was allowed to cool down to ambient temperature. The suspension was aged and the solid was filtered off. The filter cake was rinsed with a mixture of 2-propanol (20 mL) and isopropyl ether (20 ml), and dried to afford 4-oxopiperidine methyl N-cyanothioimidocarbamate (14, 17.94 g, 88% yield) as an off-white solid.

$^1$H NMR (400 MHz, CDCl$_3$) δ 4.11 (t, J=6.4 Hz, 4H), 2.85 (s, 3H), 2.60 (t, J=6.3 Hz, 4H) ppm.

$^{13}$C NMR (100 MHz, CDCl$_3$) δ 204.8, 169.7, 114.5, 46.4, 40.2, 16.4 ppm.

Example 5

Preparation of methyl (2)-4-((2S,5S)-5-(4-chlorobenzyl)-2-methylmorpholino)-N-cyanopiperidine-1-carbimidothioate (6) Directly from (2S,5S)-5-(4-chlorobenzyl)-2-methylmorpholine (2)

(2S,5S)-5-(4-Chlorobenzyl)-2-methylmorpholine (2, 5.23 g), 4-oxopiperidine methyl N-cyanothioimidocarbamate (14, 6.86 g) and zinc chloride (3.16 g) were suspended in ethanol (52 ml). The slightly cloudy solution was cooled down to 0° C. and sodium cyanoborohydride (2.19 g) was added portionwise. The suspension was stirred at ambient temperature for 24 h. The reaction was quenched by addition of 1 M solution of sodium hydroxide (60 mL) and extracted with dichloromethane (60 mL, then 2×30 ml). The combined organic layers were washed with water (30 mL) and the solvent was swapped to ethanol. During the swap the product precipitated. The suspension was allowed to cool down to ambient temperature and the solid was filtered off. The filter cake was rinsed with ethanol (18 mL) and dried to afford methyl (Z)-4-((2S,5S)-5-(4-chlorobenzyl)-2-methylmorpholino)-N-cyanopiperidine-1-carbimidothioate (6, 7.80 g, 83% yield, 99.5% purity by HPLC) as an off-white solid.

$^1$H NMR (400 MHz, CDCl$_3$) δ 7.28-7.22 (m, 2H), 7.13-7.08 (m, 2H), 4.45-4.34 (m, 2H), 3.68-3.54 (m, 2H), 3.46 (dd, J=11.5, 2.7 Hz, 1H), 3.32 (dd, J=12.1, 2.8 Hz, 2H), 3.01 (dd, J=12.9, 10.8 Hz, 1H), 2.88-2.77 (m, 2H), 2.76 (s, 3H), 2.71-2.62 (m, 2H), 2.36 (dd, J=11.8, 10.3 Hz, 1H), 2.07-1.94 (m, 2H), 1.68-1.47 (m, 2H), and 1.21 (d, J=6.2 Hz, 3H) ppm.

$^{13}$C NMR (100 MHz, CDCl$_3$) δ 168.7, 138.3, 132.0, 130.8, 128.8, 115.4, 72.5, 67.8, 55.8, 55.4, 50.0, 46.9, 30.3, 29.8, 27.5, 19.3, and 16.4 ppm.

FT-IR (ATR): 2959, 2926, 2866, 2820, 2795, 2167, 1541, 1491, 1450, 1431, 1383, 1358, 1273, 1215, 1151, 1117, 1096, 1070, 1043, 1013, 988, 930, 862, 833, 806, 714, 665, and 638 cm$^{-1}$.

Example 6

Preparation of 5-(4-((2S,5S)-5-(4-chlorobenzyl)-2-methylmorpholino)piperidin-1-yl)-4H-1,2,4-triazol-3-amine hydrated Form I (1, hydrated Form I) from (2S,5S)-5-(4-chlorobenzyl)-2-methyl-4-(piperidin-4-yl)morpholine dihydrochloride hydrate (5, dihydrochloride hydrate)

(2S,5S)-5-(4-Chlorobenzyl)-2-methyl-4-(piperidin-4-yl) morpholine dihydrochloride hydrate (5, dihydrochloride hydrate, 9.03 g) and dimethyl N-cyanodithioiminocarbonate (3.80 g) were suspended in 1-propanol (72 ml). Triethylamine (9.9 mL) was added and the clear solution was refluxed for 3 hours. Hydrazine monohydrate (3.5 mL) was added and the reaction was further carried out at 60° C. for additional 2 hours. Water (144 mL) was added to the hot solution that was allowed to cool down to ambient temperature, seeded with a crystalline material and put into a refrigerator for 24 hours. The precipitate was filtered off and the filter cake was rinsed with water (2×40 mL) and dried in the air to afford crude product (14.3 g) as 5-(4-((2S,5S)-5-(4-chlorobenzyl)-2-methylmorpholino)piperidin-1-yl)-4H-1,2,4-triazol-3-amine hydrated form I (1, hydrated form I, 7.06 g, 25% loss on drying, 80% yield on dry basis, 99.4% purity by HPLC) as a white solid.

The seed crystalline material used was obtained from the crude reaction mixture. The reaction mixture was concentrated to dryness under reduced pressure and the residue was purified by chromatography on silica (EtOAc:MeOH 1:0→200:1→100:1→50:1→20:1→10:1). The fractions containing the product were combined and concentrated to dryness under reduced pressure. The residue was dissolved in acetonitrile (10 mL/1 g of the product) at reflux. The solution was allowed to cool down to ambient temperature to precipitate the product. The solid was filtered off and rinsed with acetonitrile to afford the seed.

$^1$H NMR (500 MHz, CD$_3$OD) δ 7.29-7.25 (m, 2H), 7.21-7.16 (m, 2H), 3.67-3.54 (m, 2H), 3.47 (d, J=11.5 Hz, 1H), 3.01-2.72 (m, 6H), 2.72-2.63 (m, 1H), 2.35 (dd, J=12.0, 10.5 Hz, 1H), 2.10-1.95 (m, 2H), 1.58-1.39 (m, 2H), and 1.19 (d, J=6.2 Hz, 3H) ppm.

$^{13}$C NMR (125 MHz, CD$_3$OD) δ 140.1, 132.9, 132.0, 129.6, 73.7, 68.5, 57.6, 56.7, 50.9, 46.7, 30.4, 29.9, 28.1, and 19.4 ppm.

FT-IR (ATR): 3318, 3206, 2963, 2934, 2859, 2833, 1636, 1589, 1553, 1489, 1462, 1404, 1346, 1314, 1277, 1250, 1151, 117, 1092, 1069, 1013, 917, 868, 829, 800, 764, 725, and 673 cm$^{-1}$.

Example 7

Preparation of 5-(4-((2S,5S)-5-(4-chlorobenzyl)-2-methylmorpholino)piperidin-1-yl)-4H-1,2,4-triazol-3-amine hydrated Form I (1, hydrated Form I) from methyl (Z)-4-((2S,5S)-5-(4-chlorobenzyl)-2-methylmorpholino)-N-cyanopiperidine-1-carbimidothioate (6)

Methyl (Z)-4-((2S,5S)-5-(4-chlorobenzyl)-2-methylmorpholino)-N-cyanopiperidine-1-carbimidothioate (6, 7.51 g) was suspended in ethanol (37 mL) and hydrazine hydrate (2.67 mL) was added. The suspension was heated up to 60° C. and a clear solution was obtained. After 2 h water (113 mL) was added and the product precipitated upon cooling to ambient temperature. The solid was filtered off and the filter cake was rinsed with water (37 mL), and dried to afford 5-(4-((2S,5S)-5-(4-chlorobenzyl)-2-methylmorpholino)piperidin-1-yl)-4H-1,2,4-triazol-3-amine hydrated form I (1, hydrated form I, 15.82 g, 36% loss on drying, 133% yield, 99.7% purity by HPLC) as a white solid.

$^1$H NMR (500 MHz, CD$_3$OD) δ 7.29-7.25 (m, 2H), 7.21-7.16 (m, 2H), 3.67-3.54 (m, 2H), 3.47 (d, J=11.5 Hz, 1H), 3.01-2.72 (m, 6H), 2.72-2.63 (m, 1H), 2.35 (dd, J=12.0, 10.5 Hz, 1H), 2.10-1.95 (m, 2H), 1.58-1.39 (m, 2H), and 1.19 (d, J=6.2 Hz, 3H) ppm.

$^{13}$C NMR (125 MHz, CD$_3$OD) δ 140.1, 132.9, 132.0, 129.6, 73.7, 68.5, 57.6, 56.7, 50.9, 46.7, 30.4, 29.9, 28.1, and 19.4 ppm.

FT-IR (ATR): 3318, 3206, 2963, 2934, 2859, 2833, 1636, 1589, 1553, 1489, 1462, 1404, 1346, 1314, 1277, 1250, 1151, 117, 1092, 1069, 1013, 917, 868, 829, 800, 764, 725, and 673 cm$^{-1}$.

Example 8

Preparation of 5-(4-((2S,5S)-5-(4-chlorobenzyl)-2-methylmorpholino)piperidin-1-yl)-4H-1,2,4-triazol-3-amine anhydrous Form (1, anhydrous Form) from 5-(4-((2S,5S)-5-(4-chlorobenzyl)-2-methylmorpholino)piperidin-1-yl)-4H-1,2,4-triazol-3-amine hydrated Form I (1, hydrated Form 1)

5-(4-((2S,5S)-5-(4-Chlorobenzyl)-2-methylmorpholino)piperidin-1-yl)-4H-1,2,4-triazol-3-amine hydrated form I (1, hydrated form I, 6.62 g calculated on dry basis) was suspended in ethyl acetate (66 mL) and the suspension was heated up to reflux. Upon heating, the suspension turned into a clear solution. Water was distilled off using a Dean-Stark trap until boiling point of 76° C. was reached. During the distillation the product precipitated. The suspension was allowed to cool down to ambient temperature and the solid was filtered off. The filter cake was rinsed with ethyl acetate (13 mL) and dried to afford 5-(4-((2S,5S)-5-(4-chlorobenzyl)-2-methylmorpholino)pipe-ridin-1-yl)-4H-1,2,4-triazol-3-amine anhydrous form (1, anhydrous form, 6.38 g, 83% yield, >99.9% purity by HPLC) as white crystals.

$^1$H NMR (700 MHz, C$_6$D$_6$/CD$_3$OD) δ 7.13 (d, J=8.2 Hz, 2H), 6.89 (d, J=8.2 Hz, 2H), 3.99 (br s, 2H), 3.66 (br s, 3H), 3.56 (d, J=11.4 Hz, 1H), 3.54-3.46 (m, 1H), 3.37 (d, J=11.4 Hz, 1H), 2.90-2.80 (m, 3H), 2.68 (d, J=10.4 Hz, 1H), 2.40 (d, J=11.9 Hz, 2H), 2.32-2.25 (m, 1H), 2.05 (t, J=11.2 Hz, 1H), 1.81 (d, J=12.5 Hz, 1H), 1.65 (d, J=12.5 Hz, 1H), 1.54-1.46 (m, 1H), 1.46-1.37 (m, 1H), and 1.11 (d, J=6.2 Hz, 3H) ppm.

$^{13}$C NMR (175 MHz, C$_6$D$_6$) δ 139.0, 132.1, 131.2, 129.0, 128.1, 72.6, 67.8, 56.5, 55.7, 50.1, 48.9, 45.8, 45.7, 29.7, 29.2, 27.7, and 19.3 ppm.

FT-IR (ATR): 3252, 3198, 3119, 2955, 2924, 2857, 2793, 1666, 1599, 1543, 1483, 1456, 1404, 1337, 1283, 1248, 1136, 1117, 1094, 1072, 1053, 1013, 908, 858, 795, and 718 cm$^{-1}$.

Example 9

Preparation of 5-(4-((2S,5S)-5-(4-chlorobenzyl)-2-methylmorpholino)piperidin-1-yl)-4H-1,2,4-triazol-3-amine anhydrous Form (1, anhydrous form) from methyl (2)-4-((2S,5S)-5-(4-chlorobenzyl)-2-methylmorpholino)-N-cyanopiperidine-1-carbimidothioate (6)

Methyl (Z)-4-((2S,5S)-5-(4-chlorobenzyl)-2-methylmorpholino)-N-cyanopiperidine-1-carbimidothioate (6, 5.05 g) was suspended in acetonitrile (50 mL) and hydrazine hydrate (1.78 mL) was added. The suspension was heated up to 60° C. and clear solution was obtained. After 2 h, the solution was allowed to cool down to ambient temperature and the product precipitated. The solid was filtered off, and the filter cake was rinsed with acetonitrile (12.5 mL) to afford 5-(4-((2S,5S)-5-(4-chlorobenzyl)-2-methylmorpholino)piperidin-1-yl)-4H-1,2,4-triazol-3-amine anhydrous form (1, anhydrous form, 4.39 g, 90% yield, 98.7% purity by HPLC) as white crystals.

$^1$H NMR (700 MHz, C$_6$D$_6$/CD$_3$OD) δ 7.13 (d, J=8.2 Hz, 2H), 6.89 (d, J=8.2 Hz, 2H), 3.99 (br s, 2H), 3.66 (br s, 3H), 3.56 (d, J=11.4 Hz, 1H), 3.54-3.46 (m, 1H), 3.37 (d, J=11.4 Hz, 1H), 2.90-2.80 (m, 3H), 2.68 (d, J=10.4 Hz, 1H), 2.40 (d, J=11.9 Hz, 2H), 2.32-2.25 (m, 1H), 2.05 (t, J=11.2 Hz, 1H), 1.81 (d, J=12.5 Hz, 1H), 1.65 (d, J=12.5 Hz, 1H), 1.54-1.46 (m, 1H), 1.46-1.37 (m, 1H), and 1.11 (d, J=6.2 Hz, 3H) ppm.

$^{13}$C NMR (175 MHz, C$_6$D$_6$) δ 139.0, 132.1, 131.2, 129.0, 128.1, 72.6, 67.8, 56.5, 55.7, 50.1, 48.9, 45.8, 45.7, 29.7, 29.2, 27.7, and 19.3 ppm.

FT-IR (ATR): 3252, 3198, 3119, 2955, 2924, 2857, 2793, 1666, 1599, 1543, 1483, 1456, 1404, 1337, 1283, 1248, 1136, 1117, 1094, 1072, 1053, 1013, 908, 858, 795, and 718 cm$^{-1}$.

Example 10

Preparation of 5-(4-((2S,5S)-5-(4-chlorobenzyl)-2-methylmorpholino)piperidin-1-yl)-4H-1,2,4-triazol-3-amine hydrated Form II (1, hydrated form II) from 5-(4-((2S,5S)-5-(4-chlorobenzyl)-2-methylmorpholino)piperidin-1-yl)-4H-1,2,4-triazol-3-amine anhydrous Form (1, anhydrous Form)

5-(4-((2S,5S)-5-(4-Chlorobenzyl)-2-methylmorpholino)piperidin-1-yl)-4H-1,2,4-triazol-3-amine anhydrous form (1, anhydrous form, 5.03 g) was dissolved in methanol (20 mL) at reflux. Water (30 mL) was slowly added maintaining the reflux. Upon addition the product precipitated. The suspension was allowed to cool down to ambient temperature and was aged for an hour. The solid was filtered off and the filter cake was rinsed with a mixture of methanol and water (25 mL, 2:3 vol./vol.), and dried in the air overnight to afford 5-(4-((2S,5S)-5-(4-chlorobenzyl)-2-methylmorpholino)piperidin-1-yl)-4H-1,2,4-triazol-3-amine hydrated form II (1, hydrated form II, 5.44 g, 8.2% water by Karl-Fischer, 99% yield on dry basis, >99.9% purity by HPLC) as a white solid.

Example 11

Preparation of 5-(4-((2S,5S)-5-(4-chlorobenzyl)-2-methylmorpholino)piperidin-1-yl)-4H-1,2,4-triazol-3-amine amorphous Form (1, amorphous Form) from 5-(4-((2S,5S)-5-(4-chlorobenzyl)-2-methylmorpholino)piperidin-1-yl)-4H-1,2,4-triazol-3-amine anhydrous Form (1, anhydrous Form)

A Petri dish covered with 5-(4-((2S,5S)-5-(4-chlorobenzyl)-2-methylmorpholino)piperidin-1-yl)-4H-1,2,4-triazol-3-amine anhydrous form (1, anhydrous form, 5.02 g) was placed on a hot-plate heated up to 200° C. When the material melted, the dish was allowed to cool down to ambient temperature. The glass-like material was ground in a mortar to afford 5-(4-((2S,5S)-5-(4-chlorobenzyl)-2-methylmorpholino)piperidin-1-yl)-4H-1,2,4-triazol-3-amine amorphous form (1, amorphous form, 4.82 g, 96% yield, >99.9% purity by HPLC) as a white solid.

$^1$H NMR (700 MHz, C$_6$D$_6$/CD$_3$OD) δ 7.13 (d, J=8.2 Hz, 2H), 6.89 (d, J=8.2 Hz, 2H), 3.99 (br s, 2H), 3.66 (br s, 3H), 3.56 (d, J=11.4 Hz, 1H), 3.54-3.46 (m, 1H), 3.37 (d, J=11.4 Hz, 1H), 2.90-2.80 (m, 3H), 2.68 (d, J=10.4 Hz, 1H), 2.40 (d, J=11.9 Hz, 2H), 2.32-2.25 (m, 1H), 2.05 (t, J=11.2 Hz, 1H), 1.81 (d, J=12.5 Hz, 1H), 1.65 (d, J=12.5 Hz, 1H), 1.54-1.46 (m, 1H), 1.46-1.37 (m, 1H), and 1.11 (d, J=6.2 Hz, 3H) ppm.

$^{13}$C NMR (175 MHz, C$_6$D$_6$) δ 139.0, 132.1, 131.2, 129.0, 128.1, 72.6, 67.8, 56.5, 55.7, 50.1, 48.9, 45.8, 45.7, 29.7, 29.2, 27.7, and 19.3 ppm.

FT-IR (ATR): 3312, 3173, 2968, 2859, 2822, 1634, 1551, 1489, 1458, 1346, 1277, 1246, 1150, 1115, 1094, 1069, 1013, 920, 858, 804, 758, 719, and 665 cm$^{-1}$.

Example 12

Preparation of 5-(4-((2S,5S)-5-(4-chlorobenzyl)-2-methylmorpholino)piperidin-1-yl)-4H-1,2,4-triazol-3-amine amorphous Form (1, amorphous Form) from 5-(4-((2S,5S)-5-(4-chlorobenzyl)-2-methylmorpholino)piperidin-1-yl)-4H-1,2,4-triazol-3-amine hydrated Form I or II (1, hydrated Form I or II)

A Petri dish covered with 5-(4-((2S,5S)-5-(4-chlorobenzyl)-2-methylmorpholino)piperidin-1-yl)-4H-1,2,4-triazol-3-amine hydrated form I or II (1, hydrated form I or II, 5.01 g) was placed on a hot-plate heated up to 125° C. When the material melted, the dish was allowed to cool down to ambient temperature. The glass-like material was ground in a mortar to afford 5-(4-((2S,5S)-5-(4-chlorobenzyl)-2-methylmorpholino)piperidin-1-yl)-4H-1,2,4-triazol-3-amine amorphous form (1, amorphous form, 4.49 g, 90% yield, >99.99% purity by HPLC starting from hydrated form I, and 1, amorphous form, 4.41 g, 88% yield, >99.9% purity by HPLC starting from hydrated form II) as a white solid.

$^1$H NMR (700 MHz, C$_6$D$_6$/CD$_3$OD) δ 7.13 (d, J=8.2 Hz, 2H), 6.89 (d, J=8.2 Hz, 2H), 3.99 (br s, 2H), 3.66 (br s, 3H), 3.56 (d, J=11.4 Hz, 1H), 3.54-3.46 (m, 1H), 3.37 (d, J=11.4 Hz, 1H), 2.90-2.80 (m, 3H), 2.68 (d, J=10.4 Hz, 1H), 2.40 (d, J=11.9 Hz, 2H), 2.32-2.25 (m, 1H), 2.05 (t, J=11.2 Hz, 1H), 1.81 (d, J=12.5 Hz, 1H), 1.65 (d, J=12.5 Hz, 1H), 1.54-1.46 (m, 1H), 1.46-1.37 (m, 1H), and 1.11 (d, J=6.2 Hz, 3H) ppm.

$^{13}$C NMR (175 MHz, C$_6$D$_6$) δ 139.0, 132.1, 131.2, 129.0, 128.1, 72.6, 67.8, 56.5, 55.7, 50.1, 48.9, 45.8, 45.7, 29.7, 29.2, 27.7, and 19.3 ppm.

FT-IR (ATR): 3312, 3173, 2968, 2859, 2822, 1634, 1551, 1489, 1458, 1346, 1277, 1246, 1150, 1115, 1094, 1069, 1013, 920, 858, 804, 758, 719, and 665 cm$^{-1}$.

What is claimed is:
1. A process for the preparation of 5-(4-((2S,5S)-5-(4-chlorobenzyl)-2-methylmorpholino)piperidin-1-yl)-1H-1,2,4-triazol-3-amine of formula 1,

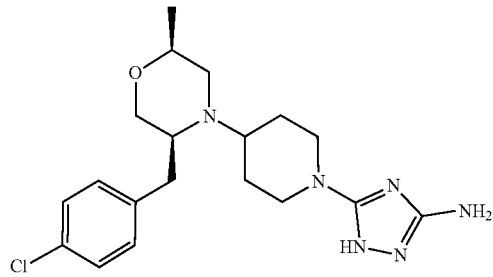

1 comprising:
a) reaction of the compound of formula 5 with dimethyl N-cyanodithioiminocarbonate in the presence of a base in a solvent, leading to (Z)-4-((2S,5S)-5-(4-chlorobenzyl)-2-methylmorpholino)-N-cyanopiperidine-1-carbimidothioate of formula 6;
wherein formula 5 is:

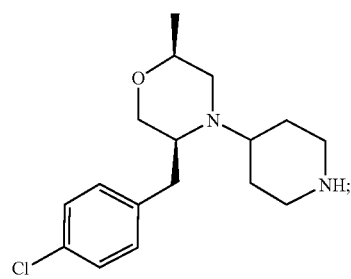

5 wherein formula 6 is:

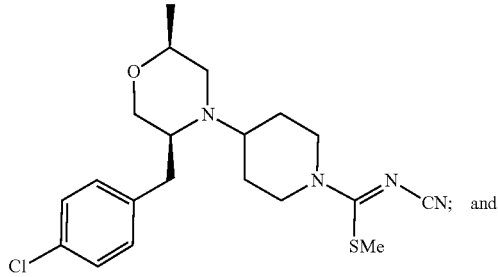

b) reaction of the compound of formula 6 with hydrazine monohydrate in acetonitrile, to provide the compound of formula 1;

wherein the compound of formula 6 is isolated after step (a) and before step (b).

2. The process of claim 1, wherein in step (a) the compound of formula 5 is in a salt form.

3. The process of claim 1, further comprising:

(a') reacting (2S,5S)-5-(4-chlorobenzyl)-2-methylmorpholine of formula 2

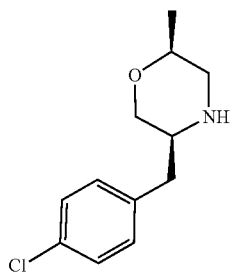

with N-Boc-4-piperidinone of formula 3

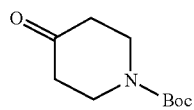

and sodium cyanoborohydride in an alcohol as a solvent, to provide tert-butyl 4-((2S,5S)-5-(4-chlorobenzyl)-2-methylmorpholino)piperidine-1-carboxylate of formula 4

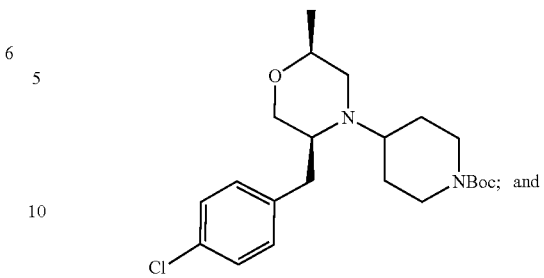

(b') removing the tert-butoxycarbonyl protecting group on the compound of formula 4 using hydrochloric acid to provide (2S,5S)-5-(4-chlorobenzyl)-2-methyl-4-(piperidin-4-yl)morpholine of formula 5.

4. The process of claim 3, wherein in step (a') the compound of formula 2 is used as its hydrochloride salt, and/or wherein in step (a') zinc chloride is added; and/or wherein in step (a') methanol is used as a solvent and/or wherein in step (b') ethyl acetate is used as a solvent.

5. The process of claim 1, wherein in step (a) the base is a trialkylamine.

6. The process of claim 5, wherein the base is triethylamine.

7. The process of claim 1, wherein in step (a) the solvent is ethanol, 1-propanol, 2-propanol, or acetonitrile.

8. The process of claim 1, wherein in step (a) the solvent is ethanol, 1-propanol or 2-propanol; and the compound of formula 6 is isolated after step (a) by precipitation upon cooling of the reaction mixture.

9. The process of claim 2, wherein in step (a) the solvent is ethanol, 1-propanol or 2-propanol; and the compound of formula 6 is isolated after step (a) by precipitation upon cooling of the reaction mixture.

10. The process of claim 1, wherein in step (a) the solvent is ethanol, 1-propanol or 2-propanol; and the compound 1 is isolated after step (b) by precipitation upon addition of water to the reaction mixture.

11. The process of claim 1, wherein in step (a) the solvent is acetonitrile; and the compound of formula 1 is isolated after step (b) by precipitation upon cooling of the reaction mixture.

12. The process of claim 1, wherein without chromatographic purification the compound of formula 1 is obtained in ≥99.0%, ≥99.1%, ≥99.2%, ≥99.3%, ≥99.4%, ≥99.5%, ≥99.6%, ≥99.7%, ≥99.8%, ≥99.9%, ≥99.92%, or ≥99.95% purity.

13. The process of claim 1, wherein without chromatographic purification the compound of formula 1 has a level of residual hydrazine less than 0.5 ppm, 0.4 ppm, 0.3 ppm, 0.2 ppm, or 0.1 ppm.

14. The process of claim 1, wherein without chromatographic purification the compound of formula 1 has a particle size distribution D10≤202 μm, D50≤357 μm, and D90≤577 μm.

* * * * *

UNITED STATES PATENT AND TRADEMARK OFFICE
CERTIFICATE OF CORRECTION

PATENT NO. : 11,746,107 B2
APPLICATION NO. : 17/032232
DATED : September 5, 2023
INVENTOR(S) : Grzegorz Witkowski et al.

It is certified that error appears in the above-identified patent and that said Letters Patent is hereby corrected as shown below:

On the Title Page

Item (56) under OTHER PUBLICATIONS, right Column, Line 16, please replace:
"Onco Arendi"
With:
--OncoArendi--

Item (56) under OTHER PUBLICATIONS, right Column, Line 29, please replace:
"Pierwsky selecktywny"
With:
--Pierwszy selektywny--

Item (56) under OTHER PUBLICATIONS, right Column, Line 36, please replace:
"Onco Arendi"
With:
--OncoArendi--

Item (56) under OTHER PUBLICATIONS, right Column, Line 40, please replace:
"Onco Arendi"
With:
--OncoArendi--

Item (56) under OTHER PUBLICATIONS, right Column, Line 48, please replace:
"Onco Arendi"
With:
--OncoArendi--

Item (56) under OTHER PUBLICATIONS, right Column, Line 51, please replace:
"Onco Arendi"
With:

Signed and Sealed this
Fifth Day of March, 2024

Katherine Kelly Vidal
*Director of the United States Patent and Trademark Office*

--OncoArendi--

On Page 2, Item (56) under OTHER PUBLICATIONS, left Column, Line 10, please replace:
"Onco Arendi"
With:
--OncoArendi--

On Page 2, Item (56) under OTHER PUBLICATIONS, left Column, Line 15, please replace:
"Onco Arendi"
With:
--OncoArendi--

On Page 2, Item (56) under OTHER PUBLICATIONS, left Column, Line 19, please replace:
"Niedsiejko"
With:
--Niedziejko--

On Page 2, Item (56) under OTHER PUBLICATIONS, left Column, Line 20, please replace:
"amcase"
With:
--AMCase--

On Page 2, Item (56) under OTHER PUBLICATIONS, left Column, Line 21, please replace:
"Onco Arendi"
With:
--OncoArendi--

On Page 2, Item (56) under OTHER PUBLICATIONS, right Column, Line 1, please replace:
"Niedsiejko"
With:
--Niedziejko--

On Page 2, Item (56) under OTHER PUBLICATIONS, right Column, Line 2, please replace:
"Onco Arendi"
With:
--OncoArendi--

On Page 2, Item (56) under OTHER PUBLICATIONS, right Column, Line 6, please replace:
"Onco Arendi"
With:
--OncoArendi--

On Page 2, Item (56) under OTHER PUBLICATIONS, right Column, Line 9, please replace:
"Onco Arendi"
With:
--OncoArendi--

CERTIFICATE OF CORRECTION (continued)
U.S. Pat. No. 11,746,107 B2

On Page 2, Item (56) under OTHER PUBLICATIONS, right Column, Line 12, please replace:
"Onco Arendi"
With:
--OncoArendi--

In the Specification

At Column 3, Line 1, please replace:
"Is"
With:
--is--

At Column 4, Line 20, please replace:
"C."
With:
--C,--

At Column 4, Line 40, please replace:
"C."
With:
--C,--

At Column 4, Line 59, please replace:
"C. and a peak at 177.59+ C."
With:
--C, and a peak at 177.59° C.--

At Column 5, Line 12, please replace:
"C."
With:
--C,--

At Column 5, Line 13, please replace:
"C."
With:
--C,--

At Column 6, Line 59, please replace:
"C."
With:
--C,--

At Column 7, Line 49, please replace:
"A crucial step in the synthesis of the compound formula"
With:
--A crucial step in the synthesis of the compound of formula--

CERTIFICATE OF CORRECTION (continued)
U.S. Pat. No. 11,746,107 B2

At Column 11, Line 13, please replace:
"C."
With:
--C,--

At Column 12, Line 17, please replace:
"C."
With:
--C,--

At Column 12, Line 48, please replace:
"C."
With:
--C,--

At Column 12, Line 58, please replace:
"C."
With:
--C,--

At Column 12, Line 61, please replace:
"C."
With:
--C,--

At Column 14, Line 3, please replace:
"C."
With:
--C,--

At Column 14, Line 4, please replace:
"The solid as aged and filtered off."
With:
--The solid was aged and filtered off.--

At Column 14, Line 16, please replace:
"of formula 1 hydrated form I used from structure"
With:
--of formula 1 hydrated form I used for structure--

At Column 14, Line 44, please replace:
"$CD_3Cl$"
With:
--$Si(CH_3)_4$--

At Column 14, Line 47, please replace:
"NMR)."
With:
--NMR.--

At Column 15, Line 1, please replace:
"Cu CuKα"
With:
--CuKα--

At Column 15, Line 9, please replace:
"C./min"
With:
--C/min--

At Column 15, Line 14, please replace:
"C.,"
With:
--C,--

At Column 15, Line 36, please replace:
"C.,"
With:
--C,--

At Column 16, Line 1, please replace:
"hydrochloric add"
With:
--hydrochloric acid--

At Column 16, Line 57, please replace:
"86%%"
With:
--86%--

At Column 18, Line 8, please replace:
"Directly"
With:
--directly--

At Column 18, Line 15, please replace:
"C."
With:
--C,--

CERTIFICATE OF CORRECTION (continued)
U.S. Pat. No. 11,746,107 B2

At Column 18, Line 58, please replace:
"C."
With:
--C,--

At Column 19, Line 36, please replace:
"C."
With:
--C,--

At Column 20, Line 5, please replace:
"C."
With:
--C,--

At Column 20, Line 44, please replace:
"C."
With:
--C,--